US011865181B2

(12) United States Patent
Shrader et al.

(10) Patent No.: US 11,865,181 B2
(45) Date of Patent: Jan. 9, 2024

(54) PEPTIDIC MATERIALS THAT TRAFFIC EFFICIENTLY TO THE CELL CYTOSOL AND NUCLEUS

(71) Applicant: Yale University, New Haven, CT (US)

(72) Inventors: Alanna Schepartz Shrader, New Haven, CT (US); Kim Quach, New Haven, CT (US)

(73) Assignee: Yale University

( * ) Notice: Subject to any disclaimer, the term of this patent is extended or adjusted under 35 U.S.C. 154(b) by 459 days.

(21) Appl. No.: 16/761,364

(22) PCT Filed: Nov. 2, 2018

(86) PCT No.: PCT/US2018/058835
§ 371 (c)(1),
(2) Date: May 4, 2020

(87) PCT Pub. No.: WO2019/090015
PCT Pub. Date: May 9, 2019

(65) Prior Publication Data
US 2020/0360529 A1 Nov. 19, 2020

Related U.S. Application Data

(60) Provisional application No. 62/581,219, filed on Nov. 3, 2017.

(51) Int. Cl.
*A61K 47/64* (2017.01)
*A61K 49/00* (2006.01)
*C07K 7/02* (2006.01)

(52) U.S. Cl.
CPC ...... *A61K 47/6455* (2017.08); *A61K 49/0041* (2013.01); *C07K 7/02* (2013.01)

(58) Field of Classification Search
CPC .... C07K 7/02; C07K 2319/10; A61K 47/645; A61K 47/6455; A61K 49/0041
See application file for complete search history.

(56) References Cited

U.S. PATENT DOCUMENTS

| 7,084,244 | B2 | 8/2006 | Gilon |
| 7,192,713 | B1 | 3/2007 | Verdine |
| 7,723,469 | B2 | 5/2010 | Walensky |
| 2005/0250680 | A1 | 11/2005 | Walensky |
| 2006/0008848 | A1 | 1/2006 | Verdine |
| 2006/0014675 | A1 | 1/2006 | Arora |
| 2007/0197772 | A1 | 8/2007 | Arora |
| 2010/0234563 | A1 | 9/2010 | Arora |
| 2013/0102524 | A1* | 4/2013 | O'Neil ............. A61K 31/145 514/2.7 |
| 2015/0031612 | A1 | 1/2015 | Schepartz |
| 2017/0342108 | A1* | 11/2017 | Yu .................. C07K 1/113 |

FOREIGN PATENT DOCUMENTS

| WO | 2009108261 | 9/2009 |
| WO | 2010033617 | 3/2010 |
| WO | 2010148335 | 12/2010 |
| WO | 2012021876 | 2/2012 |
| WO | 2014169274 | 10/2014 |
| WO | 2016151478 | 9/2016 |
| WO | 2017136652 | 8/2017 |
| WO | 2017151617 | 9/2017 |

OTHER PUBLICATIONS

Rudolph C et al. J. Biol. Chem. 2003, 278(13), 11411-11418. (Year: 2003).*
Verdine G et al. Stapled peptides for intracellular drug targets. Methods in Enzymology, 2012, 503, 3-33. (Year: 2012).*
Wender PA et al. The design, synthesis, and evaluation of molecules that enable or enhance cellular uptake: Peptoid molecular transporters. Proc Natl Acad Sci USA, 2000, 97(24), 13003-13008. (Year: 2000).*
Di Pisa et al. When cationic cell-penetrating peptides meet hydrocarbons to enhance in-cell cargo delivery. J. Peptide Science, 21(5), 356-369. (Year: 2015).*
Verdine GL and Hilinski GJ. Stapled peptides for intracellular drug targets. Methods Enzymology, 503, 3-33. (Year: 2012).*
Verdurmen WPR and Brock R. Biological responses towards cationic peptides and drug carriers. Trends Pharmacological Sciences, 32(2), 116-124. (Year: 2011).*
Appelbaum, Jacob S et al. "Arginine topology controls escape of minimally cationic proteins from early endosomes to the cytoplasm." Chemistry & biology 201219,7 : 819-30. doi: 10.1016/j.chembiol.2012.05.022.
Bernal et al., "A Stapled p53 Helix Overcomes HDMX-Mediated Suppression of p53." Cancer Cell, 2010, 18, 411-422.
Bernal et al., "Reactivation of the p53 Tumor Suppressor Pathway by a Stapled p53 Peptide", J. Am. Chem. Soc., 2007, 129, 2456-2457.
Bird GH, Irimia A, Ofek G, Kwong PD, Wilson IA, Walensky LD. "Stapled HIV-1 peptides recapitulate antigenic structures and engage broadly neutralizing antibodies." Nat Struct Mol Biol. 2014;21(12):1058-1067. doi:10.1038/hsmb.2922.
Bird, Gregory H et al. "Biophysical determinants for cellular uptake of hydrocarbon-stapled peptide helices." Nature chemical biology vol. 12,10 (2016): 845-52. doi:10.1038/nchembio.2153.
Chang et al.,"Stapled α-helical peptide drug development: A potent dual inhibitor of MDM2 and MDMX for p53-dependent cancer therapy", Proc Natl Acad Sci U S A, (2013) 110, E3445-3454.
Chee SMQ, Wongsantichon J, Soo Tng Q, Robinson R, Joseph TL, et al. (2014) "Structure of a Stapled Peptide Antagonist Bound to Nutlin-Resistant Mdm2." 8 pages. PLOS ONE 9(8): e104914. https://doi.org/10.1371/journal.pone.0104914.

(Continued)

*Primary Examiner* — Kimberly Ballard
(74) *Attorney, Agent, or Firm* — Riverside Law LLP

(57) ABSTRACT

This invention is generally related to modified peptidic oligomers that have an increased ability to reach the cytosol or nucleus. In some embodiments, the modified peptidic oligomer molecules deliver an associated cargo molecule to the cytosol or nucleus. Other embodiments of the invention relate to modified peptidic oligomer fusion molecules that reach the cytosol or nucleus.

13 Claims, 9 Drawing Sheets

Specification includes a Sequence Listing.

(56) References Cited

OTHER PUBLICATIONS

Chris Philips, Lee R. Roberts, Markus Schade, Richard Bazin, Andrew Bent, Nichola L. Davies, Rob Moore, Andrew D. Pannifer, Andrew R. Pickford, Stephen H. Prior, Christopher M. Read, Andrew Scott, David G. Brown, Bin Xu, and Stephen L. Irving "Design and Structure of Stapled Peptides Binding to Estrogen Receptors", Journal of the American Chemical Society 2011 133 (25), 9696-9699.

Chu et al., "Towards understanding cell penetration by stapled peptides", Med. Chem. Commun., 2015, 6, 111-119.

Gilleron, J., Querbes, W., Zeigerer, A. et al. "Image-based analysis of lipid nanoparticle-mediated siRNA delivery, intracellular trafficking and endosomal escape." Nat Biotechnol 2013, 31, 638-646 . doi.org/10.1038/nbt.2612.

Grossmann TN, Yeh JT, Bowman BR, Chu Q, Moellering RE, Verdine GL. "Inhibition of oncogenic Wnt signaling through direct targeting of β-catenin." 6 pages. Proc Natl Acad Sci U S A. 2012; 109(44):17942-17947. doi:10.1073/pnas.1208396109.

Lama, D., Quah, S., Verma, C. et al. "Rational Optimization of Conformational Effects Induced by Hydrocarbon Staples in Peptides and their Binding Interfaces." Sci Rep 3, 3451 (2013). 10 pages. doi.org/10.1038/srep03451.

Larochelle et al., "Fluorescence Correlation Spectroscopy Reveals Highly Efficient Cytosolic Delivery of Certain Penta-Arg Proteins and Stapled Peptides", J Am Chem Soc, (Feb. 25, 2015), vol. 137, No. 7, pp. 2536-2541, XP055617796.

LaRochelle. "Fluorescence Correlation Spectroscopy Reveals Highly Efficient Cytosolic Delivery of Certain Penta-Arg Proteins and Stapled Peptides." Journal of the American Chemical Society. 137.7 (2015): 2536-2541. Web.

Leila Peraro, Zhongju Zou, Kamlesh M. Makwana, Ashleigh E. Cummings, Haydn L. Ball, Hongtao Yu, Yu-Shan Lin, Beth Levine, and Joshua A. Kritzer "Diversity-Oriented Stapling Yields Intrinsically Cell-Penetrant Inducers of Autophagy" Journal of the American Chemical Society 2017 139 (23), 7792-7802 DOI: 10.1021/jacs.7b01698.

Moellering, Raymond E et al. "Direct inhibition of the NOTCH transcription factor complex." Nature vol. 462,7270 (2009): 182-8. doi:10.1038/nature08543.

Qian et al., "Discovery and Mechanism of Highly Efficient Cyclic Cell-Penetrating Peptides" Biochemistry 2016, 55, 18, 2601-2612.

Qian et al., "Early Endosomal Escape of a Cyclic Cell-Penetrating Peptide Allows Effective Cytosolic Cargo Delivery" Biochemistry, 2014, 53, 4034-4046.

Quach et al., "Unique arginine array improves cytosolic localization of hydrocarbon-stapled peptides", Bioorganic & Medicinal Chemistry, (2017), vol. 26, No. 6, doi:10.1016/j.bmc.2017.11.008, pp. 1197-1202, XP055617788.

Sohee Baek, Peter S. Kutchukian, Gregory L. Verdine, Robert Huber, Tad A. Holak, Ki Won Lee, and Grzegorz M. Popowicz "Structure of the Stapled p53 Peptide Bound to Mdm2", Journal of the American Chemical Society 2012 134 (1), 103-106.

Speltz TE, Fanning SW, Mayne CG, et al. "Stapled Peptides with γ-Methylated Hydrocarbon Chains for the Estrogen Receptor/Coactivator Interaction." Angew Chem Int Ed Engl. 2016;55(13):4252-4255. doi:10.1002/anie.201510557.

Thompson, David B et al. "Cellular uptake mechanisms and endosomal trafficking of supercharged proteins", Chemistry & biology 2012: 19,7:831-43. doi:10.1016/j.chembiol.2012.06.014.

Walensky, Loren D. et al. "A stapled BID BH3 helix directly binds and activates BAX." Molecular cell, 2006, 24,2 : 199-210. doi:10.1016/j.molcel.2006.08.020.

Walensky, Loren D et al. "Activation of apoptosis in vivo by a hydrocarbon-stapled BH3 helix." Science (New York, N.Y.) vol. 305,5689 (2004): 1466-70. doi:10.1126/science.1099191.

Zhao et al., "Improving cell penetration of helical peptides stabilized by N-terminal crosslinked aspartic acids", Org. Biomol. Chem., 2017, 15, 459-464.

\* cited by examiner

PEPTIDIC MATERIALS THAT TRAFFIC EFFICIENTLY TO THE CELL CYTOSOL AND NUCLEUS

CROSS REFERENCE TO RELATED APPLICATIONS

This application is the U.S. national phase application filed under 35 U.S.C. § 371 claiming benefit to International Patent Application No. PCT/US2018/058835, filed on Nov. 2, 2018, which is entitled to priority under 35 U.S.C. § 119(e) to U.S. provisional application no. 62/581,219, filed Nov. 3, 2017, the disclosures of which are incorporated herein by reference in their entirety.

STATEMENT REGARDING FEDERALLY SPONSORED RESEARCH OR DEVELOPMENT

This invention was made with government support under CA170741 awarded by National Institutes of Health. The government has certain rights in the invention.

BACKGROUND OF THE INVENTION

Peptidic materials including peptide mimetics are gaining interest as therapeutics. One family of peptide mimetics with demonstrated utility as research tools and potential therapeutics are hydrocarbon-stapled peptides (Baek et al., J Am Chem Soc, 2012, 134, 103-106; Bernal et al., Cancer Cell, 2010, 18, 411-422; Moellering et al., Nature, 2009, 462, 182-188; Walensky et al., Mol. Cell, 2006, 24, 199-210). Molecules possessing an all-hydrocarbon staple resist proteolytic degradation (Schafmeister et al., J. Am. Chem. Soc., 2000, 122, 5891-5892) and can function as potent inhibitors of protein-protein interactions in cell-based assays and animals (Bernal et al., Cancer Cell, 2010, 18, 411-422; Walensky et al., Science, 2004, 305, 1466-1470). Indeed, ALRN-6924, a dual inhibitor of MDM2 and MDMX that is related to the hydrocarbon-stapled peptide ATSP-7041 (Chang et al., Proc Natl Acad Sci USA, 2013, 110, E3445-3454), is being evaluated in clinical trials (ClinicalTrials.gov identifier: NCT02264613). Other classes of macrocyclized peptides include cyclic peptides (Furukawa et al., J. Med. Chem., 2016, 59, 9503-9512; Rezai et al., J. Am. Chem. Soc., 2006, 128, 2510-2511), hydrogen-bond surrogate peptides (Patgiri et al, Acc Chem Res, 2008, 41, 1289-1300), perfluoroaryl-cysteine cross-linked peptides (Spokoyny et al., J. Am. Chem. Soc., 2013, 135, 5946-5949), and double-click stapled peptides (Lau et al., Chem. Sci., 2014, 5, 1804-1809). Yet despite the utility and promise of hydrocarbon-stapled peptides and extensive effort (Bird et al., Nat. Chem. Biol., 2016, 12, 845-852; Peraro et al., J. Am. Chem. Soc., 2017, 139, 7792-7802; Zhao et al., Org. Biomol. Chem., 2017, 15, 459-464), the physicochemical features necessary to predictably achieve high cytosolic concentration remain unknown, especially among stapled peptides possessing equivalent charge and in vitro potency (Moellering et al., Nature, 2009, 462, 182-188; Walensky et al., Science, 2004, 305, 1466-1470; Bernal et al., J. Am. Chem. Soc., 2007, 129, 2456-2457).

There is enormous interest in identifying molecules that reproducibly and efficiently deliver diverse peptidic molecules into the cytosol and nucleus of mammalian cells in culture and in animals. Some progress has been made towards determining biophysical parameters that affect overall uptake—the amount of materials that reaches any cellular compartment—but there have been no quantitative assessments of how much material actually reaches the cytosol or nucleus.

Early endocytic vesicles have been implicated in the passage of supercharged proteins (Thompson et al., Chem. Biol., 2012, 19, 831-843), cyclic peptides (Qian et al., Biochemistry, 2014, 53, 4034-4046; Qian et al., Biochemistry, 2016, 55, 2601-2612), and the contents of lipid nanoparticles (Gilleron et al., Nat. Biotechnol., 2013, 31, 638-646) into the cell interior. However, escape from early endocytic vesicles remains an obstacle to efficient delivery of peptidic molecules into the cytosol and nucleus.

Thus, there remains a need in the art for improved peptides, proteins and fusion molecules capable of efficiently crossing biological membranes with low toxicity and efficiently facilitating release of an associated protein from RabS-positive early endosomes in the cytosol. The present invention fulfills this need.

SUMMARY OF THE INVENTION

In one embodiment, the invention relates to a modified peptidic oligomer comprising at least 5 cationic residues, wherein the at least 5 cationic residues are residues at positions i, i+3, i+4, i+7, and i+8 with respect to the first cationic residue.

In one embodiment, the at least 5 cationic residues are selected from the group consisting of arginine, lysine and histidine. In one embodiment, the at least 5 cationic residues are arginine residues.

In one embodiment, the modified peptidic oligomer comprises an α-helical structure, and the at least 5 cationic residues are clustered toward the C terminus of the α-helical structure.

In one embodiment, the modified peptidic oligomer comprises at least two unnatural amino acid residues. In one embodiment, the at least two unnatural amino acid residues are selected from the group consisting of (R)-2-(7'-octenyl)alanine ($R_8$), (S)-2-(4'-pentenyl)alanine ($S_5$), (R)-2-(4'-pentenyl)alanine ($R_5$), and (S)-2-(7'-octenyl)alanine.

In one embodiment, the modified peptidic oligomer comprises a hydrocarbon staple formed between two unnatural amino acid residues.

In one embodiment, the modified peptidic oligomer comprises an amino acid sequence selected from SEQ ID NO:5 and SEQ ID NO:11.

In one embodiment, the modified peptidic oligomer is incorporated into a fusion molecule comprising a modified peptidic oligomer domain (MPOD) and a cargo domain. In one embodiment, the cargo domain comprises at least one selected from the group consisting of a small molecule, a nucleic acid and a polypeptide.

In one embodiment, the cargo domain is fused to the C-terminus of the MPOD. In one embodiment, the cargo domain is fused to the N-terminus of the MPOD.

In one embodiment, the fusion molecule further comprises a linker.

In one embodiment, the fusion molecule further comprises a label. In one embodiment, the label is a Rhodamine label.

In one embodiment, the invention relates to a composition comprising a modified peptidic oligomer comprising at least 5 cationic residues, wherein the at least 5 cationic residues are residues at positions i, i+3, i+4, i+7, and i+8 with respect to the first cationic residue, and at least one cargo molecule.

In one embodiment, the at least one cargo molecule comprises at least one selected from the group consisting of a small molecule, a nucleic acid and a polypeptide.

In one embodiment, the at least one cargo molecule is not covalently bound to the modified peptidic oligomer.

In one embodiment, the invention relates to a method of treating a disease or disorder in a subject in need thereof, the method comprising administering to the subject a therapeutically effective amount of a modified peptidic oligomer comprising at least 5 cationic residues, wherein the at least 5 cationic residues are residues at positions i, i+3, i+4, i+7, and i+8 with respect to the first cationic residue. In one embodiment, the subject is human.

In one embodiment, the invention relates to a modified peptidic oligomer comprising at least 5 cationic residues, wherein the modified peptidic oligomer comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 3, comprising FIG. 3A depicts the results of exemplary experiments demonstrating the total cell uptake as measured by flow cytometry. Bar plots illustrate relative uptake of each Rho-labeled SAH-p53-4 variant after 30 min of incubation in HeLa cells. FIG. 3B depicts representative x-z fluorescence intensity scans of individual HeLa cells following a 30-minute treatment with each Rho-labeled SAH-p53-4 variant alongside the corresponding fluorescence correlation spectroscopy (FCS) trace. FIG. 3C depicts the results of exemplary experiments demonstrating the cytosolic concentration of Rho-labeled SAH-p53-4 variant. Error bars represent S.E.M. *$P<0.05$; ****$P<0.001$; ANOVA followed by post hoc Dunnett's test. FIG. 3D depicts the results of exemplary experiments demonstrating the side-by-side comparison of total cell uptake (same data as FIG. 3A) and cytosolic concentration (same data as FIG. 3B).

DETAILED DESCRIPTION OF THE INVENTION

Figure 1:
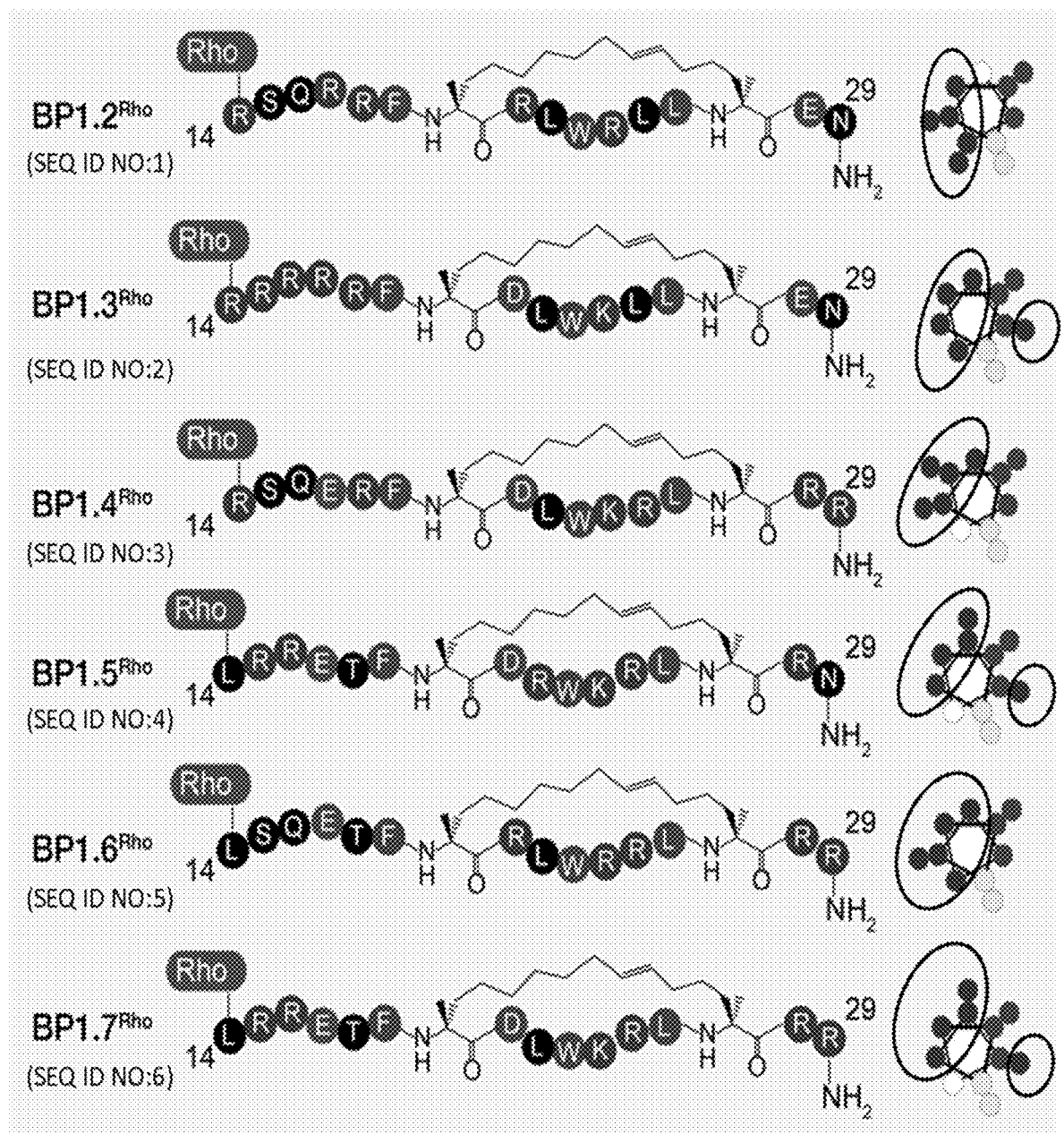
FIG. 1 depicts sequences of second-generation SAH-p53-4 variants containing diverse penta-arg motifs. The relative distribution of arginine residues (circled) is illustrated on the right with a helical wheel diagrams. The hydrocarbon staple and hDM2-binding epitope are denoted by filled, uncircled dots.

The present invention is based on the discovery that cationic modifications made to small peptidic oligomers allow them to reach the cytosol or nucleus of living cells. Certain embodiments of the invention are generally related to small peptidic oligomers comprising at least one unnatural or non-protenogenic amino acid residue which are modified so that the small peptidic oligomers reach the cytosol. In some embodiments, the modified peptidic oligomer molecules deliver an associated cargo molecule to the cytosol or nucleus. Other embodiments of the invention relate to modified peptidic oligomer fusion molecules that reach the cytosol or nucleus. In various embodiments, the modified peptidic oligomers, and fusion molecules thereof, have additional functions, such as the ability to bind to other molecules. Still other embodiments of the invention are generally directed to methods of making such modified peptidic oligomers and fusions thereof, methods of using such modified peptidic oligomers and fusions thereof, and kits comprising such modified peptidic oligomers, and fusions thereof.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, or ±5%, or ±1%, or ±0.1% from the specified value, as such variations are appropriate to perform the disclosed methods.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "housekeeping gene" as used herein refers to genes that are generally always expressed and thought to be involved in routine cellular metabolism. Housekeeping genes are well known and include such genes as glyceraldehyde-3-phosphate dehydrogenase (G3PDH or GAPDH), albumin, actins, tubulins, cyclophilin, hypoxanthine phsophoribosyltransferase (HRPT), 28S, and 18S rRNAs and the like.

"Instructional material," as that term is used herein, includes a publication, a recording, a diagram, or any other medium of expression which can be used to communicate the usefulness of the nucleic acid, polypeptide, peptide, peptidic oligomer and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "label" when used herein refers to a detectable compound or composition that is conjugated directly or indirectly to a molecule to generate a "labeled" molecule. The label may be detectable by itself (e.g. radioisotope labels or fluorescent labels) or, in the case of an enzymatic label, may catalyze chemical alteration of a substrate compound or composition that is detectable (e.g., avidin-biotin).

By the term "modulating," as used herein, is meant mediating a detectable increase or decrease in the level of a mRNA, polypeptide, or a response in a subject, or a cell or tissue of a subject, as compared with the level of a mRNA, polypeptide or a response in the subject, or a cell or tissue of the subject, in the absence of a treatment or compound, and/or compared with the level of a mRNA, polypeptide, or a response in an otherwise identical but untreated subject, or cell or tissue of the subject. The term encompasses perturbing and/or affecting a native signal or response thereby mediating a beneficial therapeutic response in a subject.

A "nucleic acid" refers to a polynucleotide and includes poly-ribonucleotides and poly-deoxyribonucleotides. Nucleic acids according to the present invention may include any polymer or oligomer of pyrimidine and purine bases, e.g., cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide or ribonucleotide component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, at least 8, at least 15 or at least 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the terms "peptide," "peptidic oligomer," "polypeptide," and "protein" are used interchangeably, and refer to a compound comprising amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. Amino acids that are included in a peptidic oligomer may be naturally occurring amino acid residues or synthetic or non-naturally occurring amino acids.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is a single strand sequence, such that amplification efficiency is optimized, but double stranded sequences can be utilized.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention generally relates to modified peptidic oligomers, and modified peptidic oligomer fusion molecules, that efficiently reach the cytosol or nucleus of living cells. Certain embodiments of the invention are generally related to modified peptidic oligomers, such as miniature proteins, including avian pancreatic polypeptide (aPP), modified such that the proteins efficiently reach the cytosol or nucleus of living cells. For instance, a portion of the aPP, such as the alpha helix region, may be modified to render the region substantially cationic. As an example, one or more residues may be substituted with cationic amino acid residues such as arginine.

The modified peptidic oligomers and fusion molecules of the invention may also have additional functions, such as the ability to bind to other proteins or polypeptides. In certain embodiments, the modified peptidic oligomer molecules deliver an associated cargo molecule to the cytosol or nucleus. Still other embodiments of the invention are generally directed to methods of making such modified peptidic oligomers, methods of using such modified peptidic oligomers, kits involving such modified peptidic oligomers, and the like.

Compositions

Various embodiments of the invention are generally directed to various modified peptidic oligomers that have been modified so that they efficiently reach the cytosol or nucleus of living cells. For example, the modified peptidic oligomers may be modified at one or more regions in a manner that causes the regions to become substantially cationic. One or more residues of a peptidic oligomer may be substituted with, for example, cationic amino acid residues. Non-limiting examples of cationic amino acid residues include arginine, lysine and histidine.

In one embodiment, the invention is a modified peptidic oligomer comprising at least 4 cationic residues. In some embodiments, the at least 4 cationic residues are selected from the group consisting of arginine, lysine and histidine. In some embodiments, the modified peptidic oligomer of the invention comprises at least 5 cationic amino acid residues, such as arginine.

In various embodiments, the modified peptidic oligomer of the invention comprises at least one selected from the group consisting of BP1.2 (SEQ ID NO:1 and SEQ ID NO:7), BP1.3 (SEQ ID NO:2 and SEQ ID NO:8), BP1.4 (SEQ ID NO:3 and SEQ ID NO:9), BP1.5 (SEQ ID NO:4 and SEQ ID NO:10), BP1.6 (SEQ ID NO:5 and SEQ ID NO:11) and BP1.7 (SEQ ID NO:6 and SEQ ID NO:12).

In one embodiment, the modified peptidic oligomer is labeled. In one embodiment, a label is Rhodamine. Rhodamine labeled modified peptidic oligomers are as set forth in SEQ ID NO:1, SEQ ID NO:2, SEQ ID NO:3, SEQ ID NO:4, SEQ ID NO:5 and SEQ ID NO:6.

In one embodiment, the modified peptidic oligomer of the invention contains at least one further modification. Modifications contemplated include, but are not limited to, acetylation, phosphorylation, methylation, or stapled amino acids, or addition of an N-terminal or C-terminal amino acid sequence including, but not limited to a polypeptide, a peptidic oligomer or a tag. In one embodiment, the modified peptidic oligomer comprise multiple modifications. Acetylated modified peptidic oligomers are as set forth in SEQ ID NO:7, SEQ ID NO:8, SEQ ID NO:9, SEQ ID NO:10, SEQ ID NO:11, and SEQ ID NO:12.

In some cases, a modified peptidic oligomer of the invention may be identified as one that efficiently reaches the cytosol or nucleus of living cells by exposing a cell to a modified peptidic oligomer and comparing the concentration of the modified peptidic oligomer within the cell after equilibration (e.g., when a steady-state concentration is reached) to the concentration of an unmodified peptidic oligomer exposed to the cell under the same conditions. A cell permeable peptidic oligomer, or fusion thereof, of the invention has a greater ability to reach the cytosol or nucleus of the cell, e.g., it can reach the cytosol or nucleus of the cell at a greater concentration than an unmodified peptidic oligomer under the same conditions. In some cases, the concentration of the modified peptidic oligomer within the cytosol or nucleus of the cell reaches a level that is greater than the concentration of an unmodified peptidic oligomer by at least about 2 times, at least about 5 times, at least about 10 times, or at least about 50 times. As a specific example, the modified peptidic oligomers may be labeled with a fluorescent entity, such as fluorescein, and their relative concentrations determined using techniques such as fluorescence correlation spectroscopy, using routine techniques known to those of ordinary skill in the art.

Positions for grafting at least 4 cationic amino acid residues on the protein scaffold include, but are not limited to, positions on the solvent-exposed alpha-helical face of a peptidic molecule. Substitutions of binding site residues may be made, in some cases, for residues involved in stabilizing the tertiary structure of the modified peptidic oligomer. As used herein, the term "exposed on the alpha helix domain" means that an amino acid substituted into a peptidic molecule is available for association or interaction with another molecule and is not otherwise bound to or associated with another amino acid residue on the peptidic molecule. This term is used interchangeably with the term "solvent-exposed alpha helical face" and similar terms (e.g., "solvent-exposed face of the alpha helix").

One embodiment of the invention is generally directed to peptic molecules that include an alpha helix region that is modified by the substitution and/or addition of various amino acid residues with cationic amino acid residues such as arginine, lysine and histidine. The modified peptidic molecules may also include other substitutions, e.g., for improving binding properties.

Cationic properties can be determined, for instance, by using charge electrophoresis or isoelectric focusing to determine the charge of the protein (or portions of the protein) under various conditions. Any number of residues within the alpha helix region may be substituted with arginine residues or the like, for instance, at least two residues, at least three residues, at least four residues, at least five residues, etc. In some cases, there may be between 3 and 6 or between 3 and 5 residues (inclusively) that are substituted with a cationic amino acid residue, such as arginine. The substitutions may be present on a single surface of the alpha helix region, and may be clustered at the N-terminal, the C-terminal or distributed along the alpha helix region. In one embodiment, at least five cationic residues are positioned at i, i+3, i+4, i+7, and i+8, with i representing the first cationic residue. In certain embodiments, the modified peptidic oligomer of the invention comprises at least one, at least two or more than three unnatural or non-proteinogenic amino acid residues. Exemplary unnatural amino acid residues that can be incorporated into the modified peptidic oligomer of the invention include, but are not limited to, (R)-2-(7'-octenyl)alanine ($R_8$), (S)-2-(4'-pentenyl)alanine ($S_5$), (R)-2-(4'-pentenyl)alanine ($R_5$), (S)-2-(7'-octenyl)alanine, D-stereoisomers of a natural amino acid residue, and amino acid analogs such as ethyl esters, methyl esters, naphthylamides, and 7-amido-4-methyl coumarin.

In certain embodiments, the modified peptidic oligomer of the invention comprises a tether, including but not limited to a hydrocarbon staple, thereby forming a "stapled peptide." In certain embodiments, the stapled peptide of the invention comprises a staple formed between two unnatural amino acids.

Hydrocarbon stapling refers to a process for stably cross-linking a polypeptide via at least two substituted amino acids (or a non-native linkage, e.g., carbon-carbon, from two natural amino acids) that helps to conformationally bestow the native secondary structure of that polypeptide. Hydrocarbon stapling promotes and maintains an alpha-helical secondary structure in peptides that thermodynamically favor an alpha-helical structure. In certain instances, this secondary structure increases resistance of the polypeptide to proteolytic cleavage and heat, and also may increase hydrophobicity. Accordingly, the hydrocarbon stapled (structurally constrained, e.g., crosslinked) peptides described herein have improved biological activity relative to a corresponding non-hydrocarbon stapled (not structurally constrained) polypeptide.

In one embodiment, the stapled peptide of the invention comprises a staple formed between two unnatural amino acids, where the unnatural amino acids comprise an olefinic side chain. Exemplary unnatural amino acids which comprise an olefinic side chain include, but are not limited to, (S)-2-(7'-octenyl)alanine, (R)-2-(7'-octenyl)alanine, (S)-2-(4'-pentenyl)alanine, and (R)-2-(4'-pentenyl)alanine. In certain embodiments, the staple is formed by an olefin metathesis reaction. However, in certain embodiments, the peptide comprises one or more unnatural amino acid having an olefinic side chain, but is "unstapled" meaning that a staple or cross-link is not formed between the unnatural amino acids.

In one embodiment, a hydrocarbon staple(s) is positioned so as to link a first amino acid and a second amino acid, with the second amino acid in a position N amino acids downstream of the first amino acid. In various embodiments, N can be 3, 4, 5, 6, 7, 8, 9, 10 or more than 10 amino acids downstream of the first stapled amino acid.

Hydrocarbon staples suitable for the present modified peptidic oligomers are described herein and in U.S. Publication Nos. 2005/0250680, 2010/0234563, 2007/0197772, 2006/0008848, 2006/0014675; U.S. Pat. Nos. 7,723,469, 7,192,713, and 7,084,244; International Publication Nos. WO 2009/108261) and WO 2010/148335; and Kawamoto, S. A. et al, J. Med. Chem. 55, 1137-1146 (2012); Mahon, A. B. and Arora, P. S., Chem. Commun. 48, 1416-1418 (2012); and Chapman, R. N. et al., J. Am. Chem. Soc. 126, 12252-3 (2004), which are incorporated by reference in their entirety. Hydrocarbon stapling allows a peptide, predisposed to have a helical secondary structure, to maintain its native helical conformation and increase its stability and efficacy.

In one embodiment, the hydrocarbon stapled peptides include a tether (linkage) between two amino acids, in which the tether significantly enhances the helical secondary structure of the peptide. Generally, the tether extends across the length of one or two helical turns (i.e., 3, 4 or 7 amino acids). Suitable tethers are described herein and in U.S. Publication Nos. 2005/0250680, 2010/0234563, 2007/0197772, 2006/0008848, 2006/0014675; U.S. Pat. Nos. 7,723,469, 7,192, 713, and 7,084,244; International Publication Nos. WO 2009/108261) and WO 2010/148335; and Kawamoto, S. A. et al., J. Med. Chem. 55, 1137-1146 (2012); Mahon, A. B. and Arora, P. S., Chem. Commun. 48, 1416-1418 (2012); and Chapman, R. N. et al., J. Am. Chem. Soc. 126, 12252-3 (2004).

In some embodiments, the modified peptidic oligomers of the invention are able to associate with (or bind to) specific sequences of DNA or other proteins. These proteins may be able to bind, for example, to DNA or other proteins with high affinity and selectivity. As used herein, the term "bind" or "binding" refers to the specific association or other specific interaction between two molecular species, such as, but not limited to, protein-DNA interactions and protein-protein interactions, for example, the specific association between proteins and their DNA targets, receptors and their ligands, enzymes and their substrates, etc. Such binding may be specific or non-specific, and can involve various noncovalent interactions such as including hydrogen bonding, metal coordination, hydrophobic forces, van der Waals forces, pi-pi interactions, and/or electrostatic effects. It is contemplated that such association may be mediated through specific sites on each of two (or more) interacting molecular species. Binding can be mediated by structural and/or energetic components. In some cases, the latter will comprise the interaction of molecules with opposite charges.

The cell permeability of the modified peptidic oligomer may be determined, for example, as previously described. Thus, for example, cells may be exposed to a concentration of 1 micromolar of modified peptidic oligomer, and the concentrations of each within the cell, or the cytosol or nucleus of the cell, may be determined in some fashion. For example, the protein may be labeled with a fluorescent entity, such as fluorescein, and the relative concentrations determined using techniques described elsewhere herein.

In one embodiment, the invention encompasses peptidic molecules that bind to other proteins or peptides and methods for making these peptidic molecules. Binding of proteins modulates protein-protein and/or protein-ligand interactions and, in some embodiments, the binding blocks the association (or specific binding) of ligands and receptors. The ligand can be another protein but also can be any other type of molecule such as a chemical substrate. In one embodiment of the present invention, making the protein-binding protein of the invention involves determining the amino acid residues which are essential to binding of the ligand protein to its target receptor protein. In some embodiments, these essential residues are identified using three-dimensional models of a protein or protein complex which binds to or interacts with another protein based on crystallographic studies while in other embodiments they are identified by studies of deletion or substitution mutants of the protein.

The modified peptidic oligomers of the present invention further include variants of the peptidic oligomers herein described. As used herein, a "variant" refers to alterations in the amino acid sequence that do not substantially and adversely affect the ability of the modified peptidic oligomer to traffic efficiently to the cytosol or nucleus. A substitution, insertion or deletion is said to adversely affect the modified peptidic oligomer when the altered sequence prevents, reduces, or disrupts ability of the modified peptidic oligomer to traffic efficiently to the cytosol or nucleus. For example, alterations that maintain in the overall charge, structure or hydrophobic-hydrophilic properties of the modified peptidic oligomer can be altered without adversely affecting an activity. Accordingly, the amino acid sequence can be altered, for example to alter the location of a cationic residue along the surface of the alpha helix, or a conservative substitution may be made to the amino acid sequence without adversely affecting the activities of the modified peptidic oligomer.

These variants, though possessing a slightly different amino acid sequence than those recited elsewhere herein, will still have the same or similar properties associated with any of the modified peptidic oligomers discussed herein. Ordinarily, the conservative substitution variants, will have an amino acid sequence having at least 75%, at least 80%, at least 85%, at least 90%, at least 95% amino acid, at least 96%, at least 97%, at least 98%, or at least 99% sequence identity with any of the modified peptidic oligomers discussed elsewhere herein.

Thus, the modified peptidic oligomers of the present invention include molecules comprising any of the amino acid sequences discussed herein, including SEQ ID NO: 1, 2, 3, 4, 5, 6, 7, 8, 9, 10, 11 and 12; or fragments thereof having a consecutive sequence of at least about 10, 11, 12, 13 or more amino acid residues of the modified peptidic oligomers of the invention; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those derivatives wherein the modified peptidic oligomer has been covalently modified by substitution, chemical, enzymatic, or other appropriate means with a moiety other than a naturally occurring amino acid (for example, a detectable moiety such as an enzyme or radioisotope).

In one embodiment, the modified peptidic oligomers of the invention can be fused to another polypeptide, peptidic oligomer or tag, such as a leader or secretory sequence or a sequence which is employed for purification or for detection. Accordingly, in one embodiment, the modified peptidic oligomer of the invention further comprises the amino acid sequence of a tag. The tag includes but is not limited to: polyhistidine tags (His-tags) (for example H6 and H10, etc.), SUMO (small ubiquitin-related modifier) fusions, GST fusions, MBP fusions, streptavidine-tags, the BSP biotinylation target sequence of the bacterial enzyme BIRA and tag epitopes that are directed by antibodies (for example c-myc tags, FLAG-tags, among others). As will be observed by a person skilled in the art, the tag peptide can be used for production, purification, inspection, selection and/or visualization of the modified peptidic oligomer of the invention. For example, in one embodiment, the modified peptidic oligomer of the invention is linked to a cleavable N-terminal His6-SUMO (small ubiquitin-related modifier) fusion tag to increase the production of the modified peptidic oligomer of the invention. In one embodiment of the invention, the tag is a detection tag and/or a purification tag. It will be appreciated that the tag sequence will not interfere in the function of the protein of the invention.

The present invention further provides, in another embodiment, nucleic acid molecules that encode any of the peptidic oligomer discussed herein, including any of SEQ ID NO: 1, 2, 3, 4, 5, 6, 7, 8, 9, 10, 11, and 12 or the related modified peptidic oligomers herein described. In one embodiment, the nucleic acid molecules are in isolated form. As used herein, "nucleic acid" includes cDNA and mRNA, as well as nucleic acids based on alternative backbones or including alternative bases whether derived from natural sources or synthesized. Those of ordinary skill in the art, given an amino acid sequence, will be able to generate corresponding nucleic acid sequences that can be used to generate the amino acid sequence, using no more than routine skill.

Modifications to the primary structure itself by deletion, addition, or alteration of the amino acids incorporated into the modified peptidic oligomer sequence during translation can be made without destroying the activity of the modified peptidic oligomer. Such substitutions or other alterations result in modified peptidic oligomers having an amino acid sequence encoded by a nucleic acid falling within the contemplated scope of the present invention.

The present invention further provides, in some embodiments, recombinant DNA molecules that contain a coding sequence. As used herein, a "recombinant DNA molecule" is a DNA molecule that has been subjected to molecular manipulation. Methods for generating recombinant DNA molecules are well known in the art, for example, see Sambrook et al., 2012, Molecular Cloning: A Laboratory Manual, Cold Spring Harbor Laboratory, New York. In some recombinant DNA molecules, a coding DNA sequence is operably linked to expression control sequences and vector sequences.

The choice of vector and expression control sequences to which one of the modified peptidic oligomer family encoding sequences of the present invention is operably linked depends directly, as is well known in the art, on the functional properties desired (e.g., protein expression, and the host cell to be transformed). A vector of the present invention may be at least capable of directing the replication or insertion into the host chromosome. In one embodiment, a vector of the present invention may be capable of expression of the structural gene included in the recombinant DNA molecule.

Expression control elements that are used for regulating the expression of an operably linked protein encoding sequence are known in the art and include, but are not limited to, inducible promoters, constitutive promoters, secretion signals, and other regulatory elements. In some embodiments, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomal in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical of bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Any suitable prokaryotic host can be used to express a recombinant DNA molecule encoding a modified peptidic oligomer of the invention.

Expression vectors compatible with eukaryotic cells, including those compatible with vertebrate cells, can also be used to form recombinant DNA molecules that contain a coding sequence. Eukaryotic cell expression vectors are well known in the art and are available from several commercial sources. Typically, such vectors are provided containing convenient restriction sites for insertion of the desired DNA segment.

Eukaryotic cell expression vectors used to construct the recombinant DNA molecules of the present invention may further include a selectable marker that is effective in a eukaryotic cell, such as a drug resistance selection marker. An example drug resistance marker is the gene whose expression results in neomycin resistance, i.e., the neomycin phosphotransferase (neo) gene. Alternatively, the selectable marker can be present on a separate plasmid, the two vectors introduced by co-transfection of the host cell, and transfectants selected by culturing in the appropriate drug for the selectable marker.

The present invention further provides, in yet another embodiment, host cells transformed with a nucleic acid molecule that encodes a modified peptidic oligomer of the present invention. The host cell can be either prokaryotic or eukaryotic. Eukaryotic cells useful for expression of a modified peptidic oligomer of the invention are not limited, so long as the cell line is compatible with cell culture methods and compatible with the propagation of the expression vector and expression of the gene product.

Transformation of appropriate cell hosts with a recombinant DNA molecule encoding a modified peptidic oligomer of the present invention is accomplished by well-known methods that typically depend on the type of vector used and host system employed. With regard to transformation of prokaryotic host cells, electroporation and salt treatment methods can be employed (see, for example, Sambrook et al., 2012, Molecular Cloning: A Laboratory Manual, Cold Spring Harbor Laboratory Press). With regard to transformation of vertebrate cells with vectors containing recombinant DNA, electroporation, cationic lipid or salt treatment methods can be employed (see, for example, Graham et al, (1973) Virology 52, 456-467; Wigler et al., (1979) Proc. Natl. Acad. Sci. USA 76, 1373-1376).

Successfully transformed cells can be identified by well-known techniques including the selection for a selectable marker. For example, cells resulting from the introduction of a recombinant DNA of the present invention can be cloned to produce single colonies. Cells from those colonies can be harvested, lysed and their DNA content examined for the presence of the recombinant DNA using a method such as that described by Southern, (1975) J. Mol. Biol. 98, 503-517 or the modified peptidic oligomers produced from the cell assayed via an immunological method.

The present invention further provides, in still another embodiment, methods for producing a modified peptidic oligomer of the invention using nucleic acid molecules herein described. In general terms, the production of a recombinant form of a modified peptidic oligomer typically involves the following steps: a nucleic acid molecule is obtained that encodes a peptidic oligomer of the invention, such as the nucleic acid molecule encoding a peptidic oligomer described herein, including a nucleic acid molecule encoding a peptidic oligomer comprising any of SEQ ID NO: 1, 2, 3, 4, 5, 6, 7, 8, 9, 10, 11 and 12.

The nucleic acid molecule may be operably linked with suitable control sequences, as described above, to form an expression unit for expression of a peptidic oligomer. The expression unit is used to transform a suitable host and the transformed host is cultured under conditions that allow the production of the recombinant modified peptidic oligomer. Optionally the recombinant peptidic oligomer may be isolated from the medium or from the cells; recovery and purification of the peptidic oligomer may not be necessary in some instances where some impurities may be tolerated.

Each of the foregoing steps can be done in a variety of ways. The construction of expression vectors that are operable in a variety of hosts is accomplished using appropriate replicons and control sequences, as set forth above. The control sequences, expression vectors, and transformation methods are dependent on the type of host cell used to express the gene. Suitable restriction sites, if not normally available, can be added to the ends of the coding sequence so as to provide an excisable gene to insert into these vectors. An artisan of ordinary skill in the art can readily adapt any host/expression system known in the art for use with the nucleic acid molecules of the invention to produce a recombinant modified peptidic oligomer.

Modified Peptidic Oligomer Fusion Molecules

The present invention relates to compositions and methods for promoting transduction of cargo molecules into the cytosol or nucleus of cells. The modified peptidic oligomer domains (MPODs) of the fusion molecule compositions described herein serve to transduce the molecules, and fusion molecules, into cells. By the term "fusion molecule" as it is used herein is meant a MPOD and a cargo domain covalently linked (i.e., fused) by recombinant, chemical or other suitable method. If desired, the fusion molecule can be fused at one or several sites through a linker sequence, such as a peptide linker sequence. In some embodiments, the fusion molecules are fusion proteins.

Modified peptidic oligomer fusion molecules having an MPOD have the property of being able to cross a cell membrane and transport a cargo domain to an intracellular compartment of a cell, including the cytosol or nucleus. MPODs of the present invention can be made by any method known in the art for synthesizing peptide fusion molecules. For example, MPODs can be synthesized chemically or can be made recombinantly.

The modified peptidic oligomer composition can be synthesized in solid or solution phase, for example, using Fmoc or tBOC chemistries (Merrifield, J. Am. Chem. Soc. 85, 2149-2154, 1963; Roberge et al., Science 269, 202-204, 1995). Peptide synthesis can be performed using manual techniques or by automation. Automated synthesis can be achieved, for example, using an Applied Biosystems 431A Peptide Synthesizer (Perkin Elmer).

Peptides can be made recombinantly by cloning a coding sequence for the peptide and expressing it in vitro. Any polynucleotide sequence that encodes a modified peptidic oligomer composition can be used. The polynucleotide sequence can be synthesized in vitro using, e.g., phosphoroamidite chemistry. Nucleic acid synthesis can be performed using manual techniques or by automation. Automated synthesis can be achieved, for example, using an Applied Biosystems 3900 DNA Synthesizer (Perkin Elmer).

In one embodiment, the MPOD comprises at least 4 cationic residues % in some embodiments, the at least 4 cationic residues are selected from the group consisting of arginine, lysine and histidine. In some embodiments, the MPOD of the invention comprises at least 5 cationic amino acid residues, such as arginine.

In various embodiments, the MPOD of the invention comprises at least one selected from the group consisting of BP1.2 (SEQ ID NO:1 and SEQ ID NO:7), BP1.3 (SEQ ID NO:2 and SEQ ID NO:8), BP1.4 (SEQ ID NO:3 and SEQ ID NO:9), BP1.5 (SEQ ID NO:4 and SEQ ID NO:10), BP1.6 (SEQ ID NO:5 and SEQ ID NO:11) and BP1.7 (SEQ ID NO:6 and SEQ ID NO:12).

As described herein, components of the fusion molecules disclosed herein, e.g., a transducing MPOD and a cargo domain, can be organized in nearly any fashion provided that the fusion protein has the function for which it was intended. In some embodiments, each component of the fusion protein can be spaced from another component by at least one suitable linker sequence, such as a peptide linker sequence, if desired. In some embodiments, the fusion proteins may include tags, e.g., to facilitate identification and/or purification of the fusion protein.

Exemplary peptide linker sequences may comprise up from about 1 to about 30 amino acids. In some embodiments, the linker sequence is flexible so as not to hold the fusion molecule in a single rigid conformation. The linker sequence can be used, for example, to space the DNA binding protein from another domain. In some embodiments, the peptide linker sequence can be positioned between the modified peptidic oligomer domain and the cargo domain, e.g., to chemically cross-link the domains and to provide molecular flexibility.

MPODs can be synthesized in solid or solution phase, for example, using Fmoc or tBOC chemistries (Merrifield, J. Am. Chem. Soc. 85, 2149-2154, 1963; Roberge et al., Science 269, 202-204, 1995). Peptide synthesis can be performed using manual techniques or by automation. Automated synthesis can be achieved, for example, using an Applied Biosystems 431A Peptide Synthesizer (Perkin Elmer).

Peptides can be made recombinantly by cloning a coding sequence for the peptide and expressing it in vitro. Any polynucleotide sequence that encodes a MPOD can be used. The polynucleotide sequence can be synthesized in vitro using, e.g., phosphoroamidite chemistry. Nucleic acid synthesis can be performed using manual techniques or by automation. Automated synthesis can be achieved, for example, using an Applied Biosystems 3900 DNA Synthesizer (Perkin Elmer).

In some embodiments, the present invention is a nucleic acid encoding a fusion protein of the invention. When the cargo domain is a polypeptide sequence, the term fusion protein is intended to describe at least two polypeptides, typically from different sources, which are operatively linked. With regard to the polypeptides, the term "operatively linked" is intended to mean that the two polypeptides are connected in manner such that each polypeptide can serve its intended function. In some embodiments, the two polypeptides are covalently attached through peptide bonds. As discussed elsewhere herein, the two polypeptides may be separated by a peptide linker when desired.

In some embodiments, the fusion proteins described herein are produced by recombinant DNA techniques. For example, a DNA molecule encoding the first polypeptide can be ligated to another DNA molecule encoding the second polypeptide. In this instance, the resultant hybrid DNA molecule can be expressed in a suitable host cell to produce the fusion protein. The DNA molecules are ligated to each other in a 5' to 3' orientation such that, after ligation, the translational frame of the encoded polypeptides is not altered (i.e., the DNA molecules are ligated to each other in-frame). The resulting DNA molecules encode an in-frame fusion protein. The components of the fusion protein can be organized in nearly any order provided each is capable of performing its intended function. In an exemplary configuration, the C-terminus of the modified peptidic oligomer domain is operatively linked to the N-terminus of the cargo domain. That linkage can be achieved by recombinant methods if desired. However, in another configuration, the N-terminus of the modified peptidic oligomer domain is linked to the C-terminus of the cargo domain.

A MPOD-encoding polynucleotide can be inserted into an expression vector which contains the necessary elements for the transcription and translation of the inserted coding sequence. Transcription and translation control elements include, for example, a promoter (e.g., T7 or T3), ribosome binding site, start codon, stop codon, and polyadenylation site. Methods which are well known to those skilled in the art can be used to construct expression vectors containing sequences encoding MPOD-containing polypeptides and appropriate transcriptional and translational control elements. These methods include in vitro recombinant DNA techniques, synthetic techniques, and in vivo genetic recombination. Such techniques are described, for example, in Sambrook et al., 2012, Molecular Cloning: A Laboratory Manual, Cold Spring Harbor Laboratory, New York and in Ausubel et al., 1997, Current Protocols in Molecular Biology, John Wiley & Sons, New York.

A variety of expression systems are available for expressing sequences that encode a MPOD. Examples of such systems include, but are not limited to, bacteria, yeast, insect, plant, and animal cell systems. Bacteria can be transformed with recombinant bacteriophage, expression plasmids, or cosmid expression vectors. Yeast can be transformed with yeast expression vectors. Insect cells can be transfected with expression vectors or transduced with recombinant insect viruses (e.g., baculovirus). Plant cells can be transduced with recombinant plant viruses (e.g., cauliflower mosaic virus or tobacco mosaic virus). Animal cells can be transfected with expression vectors (e. g., pcDNA3 or pCMV-Sport) or transduced with recombinant viruses (e.g., retroviruses, adenoviruses, or semliki forest virus). Methods for transforming, transfecting, or transducing host cells are well-known in the art, and any appropriate method can be used.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al., 2012, Molecular Cloning: A Laboratory Manual, Cold Spring Harbor Laboratory, New York and other laboratory textbooks.

A MPOD can be purified from host cells or host cell culture medium by any method known in the art for purifying polypeptides. Examples of such methods include salt fractionation, high pressure liquid chromatography, antibody column chromatography, affinity tag column chromatography, and acrylamide gel electrophoresis. Such methods are well known to those skilled in the art.

As described elsewhere herein, the fusion molecules of the present invention are transduced into target cells or groups of such target cells. Transduction efficiency can be monitored and quantified if desired by one or a combination of different strategies. For example, one approach involves an in vitro assay that measures uptake of the fusion protein by the cell. The assay includes detectably-labeling the fusion protein with, e.g., a radioactive atom, fluorescent, phosphorescent, dexamethasone, or luminescent tag (e.g., fluorescein, rhodamine or FITC) and then measuring uptake of the labeled fusion protein. Alternatively, the fusion protein can be labeled with an enzyme capable of forming a detectable label such as horseradish peroxidase, P-galactosidase, chloramphenicol acetyl transferase or luciferase. In one embodiment, it is possible to genetically fuse a desired fusion protein to florescent protein, such as green fluorescent protein (GFP), and then assay the location of the fusion protein. Uptake can be measured by several conventional methods such as by quantifying labeled cells in a standard cell sorter (e. g., FACS), by fluorescence microscopy or by autoradiography.

The fusion molecules of the invention are capable of transducing at least about 5%, 10%, 20%, or more of the total number of target cells as determined by any methods for monitoring uptake of the fusion molecule by cells, such as FACS or related microscopical techniques. The total number of target cells can be estimated by standard techniques.

A MPOD can also be made by transcribing and translating a MPOD coding sequence in a cell-free expression system. A coding sequence for a MPOD can be linked to appropriate transcription and translation control elements by methods well known in the art. Examples of such methods include PCR, restriction enzyme digestion and ligation, and chemical synthesis. Such techniques are described, for example, in Sambrook et al., 2012, Molecular Cloning: A Laboratory Manual, Cold Spring Harbor Laboratory, New York and in Ausubel et al., 1997, Current Protocols in Molecular Biology, John Wiley & Sons, New York. Cell-free transcription and translation can be accomplished, for example, using components of rabbit reticulocyte or wheat germ extracts, which are available in kits from commercial suppliers such as Promega Corporation.

MPODs of the invention can contain conservative substitutions, i.e., exchange of one amino acid for another having similar properties. Examples of conservative substitutions include, but are not limited to, 1) glycine and alanine; 2) valine, isoleucine, and leucine; 3) aspartic acid and glutamic acid; 4) lysine and arginine; 5) asparagine and glutamine; and 6) serine and threonine.

A MPOD can be synthesized from D-or L amino acids. In addition, use of amino acid analogs is also contemplated. Examples of amino acid analogs includes, but is not limited to, ethyl esters, methyl esters, naphthylamides, and 7-amido-4-methyl coumarin.

MPODs of the present invention can also have a linker attached to the N-terminus or the C-terminus. The linker is usually 0, 1, 2, 3, 4, 5 or more amino acids in length and can be a small neutral polar or non-polar amino acid such as glycine, cysteine, serine, or threonine. An exemplary linker has an amino acid sequence Lys-Xaa-Xaa, wherein Xaa is a small neutral polar or nonpolar amino acid. In some embodiments, Xaa is glycine.

The cargo domain can be a small molecule (e.g., a radionuclide, a fluorescent marker, a dye, or a pharmaceutical agent), a protein (e.g., an immortalizing agent, an anti-apoptotic agent, an enzyme, an oncoprotein, a cell cycle regulatory protein, or an antibody), a polypeptide, a peptidic oligomer, or a nucleic acid (e.g., RNA, DNA, and cDNA). Any of these cargo domains can be pharmaceutical agents. The small molecule also can be, for example, a radionuclide, a fluorescent marker, or a dye. A polypeptide according to the invention is a polymer of amino acids comprising two or more amino acid residues and includes peptides and proteins. The polypeptide can be, for example, an immortalization protein (e.g., SV40 large T antigen and telomerase), an anti-apoptotic protein (e.g., mutant p53 and Bclx L), an antibody, an oncogene (e.g., ras, myc, HPV E6/E7, and Adenovirus E1a), a cell cycle regulatory protein (e.g., cyclin and cyclin-dependent kinase), a zinc finger nuclease (ZFN), or an enzyme (e.g., green fluorescent protein, β-galactosidase, and chloramphenicol acetyl transferase). The nucleic acid can be, e.g., RNA, DNA, or cDNA. The sequence of the nucleic acid can be a coding or a non-coding sequence (e.g., an antisense oligonucleotide). Nucleotides in the nucleic acid cargo domain can be standard nucleotides (e.g., adenosine, cytosine, guanine, thymine, inosine, and uracil) or they can be nucleotide derivatives (e.g., biotinylated nucleotide) or analogs (e.g., phosphorothioate nucleotides). For example, the nucleic acid cargo domain can be an antisense sequence comprising phosphorothioate nucleotides.

Exemplary cargo domains will have sizes conducive to the function for which those domains are intended. In various embodiments, cargo domains can be at least about 0.1, 0.2, 0. 5, 0.75, 1, 5, 10, 25, 30, 50, 100, 200, 500 kD, up to about 1000 kD or more. It should be apparent that in many cases, the size of the cargo domain dominates the size of the fusion protein.

A cargo domain can be complexed to a MPOD by any method known in the art and which is appropriate for a particular cargo domain. The skilled artisan will be able to choose the appropriate method to complex a cargo domain with a MPOD. Examples of such methods include, but are not limited to, chemical cross-linking, genetic fusion, and bridging.

A linker can be used to cross-link a MPOD with a cargo domain. The linker can be cleavable to facilitate separation of the MPOD from the cargo domain after the MPOD transports the cargo domain across a cell membrane.

The fusion molecules of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrophoresis, metal affinity columns such as Ni-NTA. See generally Sambrook et al., 2012, Molecular Cloning: A Laboratory Manual, Cold Spring Harbor Laboratory Press and Ausubel et al., 1997, Current Protocols in Molecular Biology, John Wiley & Sons, New York for disclosure relating to these methods.

In some embodiments, the fusion molecules of the present invention are part of a substantially pure preparation. That is, the fusion molecules have been isolated from cell substituents that naturally accompany it so that the fusion proteins are present in at least 80% or 90% to 95% homogeneity (w/w). Fusion molecules having at least 98 to 99% homogeneity (w/w) useful for many pharmaceutical, clinical and research applications. Once substantially purified the fusion molecule should be substantially free of contaminants for therapeutic applications. Once purified partially or to substantial purity, the fusion molecule can be used therapeutically, or in performing in vitro or in vivo assays. Substantial purity can be determined by a variety of standard techniques such as chromatography and gel electrophoresis.

Genetic fusions can be generated by linking a coding sequence for a MPOD in-frame with a coding sequence for a polypeptide cargo domain. Many methods exist in the art for linking coding sequences together. Exemplary methods include, but are not limited to, polymerase chain reaction (PCR), stitch PCR, and restriction endonuclease digestion and ligation. For example, a coding sequence for a MPOD can be added to the 5'-end of a PCR primer for a cargo domain of choice; after PCR, the coding sequences for the MPOD and the polypeptide cargo domain will be linked together. The skilled artisan will know how to ensure that the reading frames of the MPOD and the cargo domain are in frame and where transcriptional control sequences (e.g., start codon and stop codon) should be placed. A protease cleavage site can be included between the MPOD and the cargo domain. Examples of such protease cleavage sites include, but are not limited to Factor Xa and tobacco etch virus (TEV) protease.

MPODs and cargo domains can be complexed using pairs of bridging molecules. Examples of such pairs include, but are not limited to, (a) streptavidin and biotin, (b) glutathione and glutathione-S-transferase, and (c) polyhistidine and an affinity chromatography reagent (e.g., tetradentate nitrilotriacetic acid (NTA) or iminodiacetic acid (IDA)), which interact through an ion such as $Ni^{+2}$. A MPOD can be linked to either member of the pair, and a cargo is linked to the other bridging molecule. For example, if the MPOD is linked to glutathione-S-transferase then the cargo is linked to glutathione. In some embodiments, the MPOD is linked to streptavidin and the cargo is linked to biotin. The MPOD and the streptavidin can be linked by any method known in the art for linking a peptide and a bridging molecule. Examples of such methods include, but are not limited to, chemical cross-linking or genetic fusion. The cargo is then linked to biotin by any method known in the art for biotinylating small molecules, proteins, or nucleic acids, such as chemical cross-linking. The MPOD cargo domain complex can be formed by contacting the MPOD-streptavidin with the biotinylated cargo domain.

In another embodiment, glutathione and glutathione-S-transferase are used as the pair of bridging molecules. In this case, for example, the MPOD can be linked to the glutathione-S-transferase and the cargo can be linked to the glutathione. The MPOD and the glutathione-S-transferase can be linked by any method described above. The cargo is linked to the glutathione by any method known in the art for linking glutathione to small molecules, proteins, or nucleic acids. An example of such method is chemical cross-linking. The MPOD-cargo domain complex can be formed by contacting the MPOD-glutathione-S-transferase with the glutathione-linked cargo domain.

In yet another embodiment, an affinity chromatography reagent and polyhistidine are used as the pair of bridging molecules. In this case, for example, the MPOD can be linked to the affinity chromatography reagent. The affinity chromatography reagents bind ions such as $Ni^{+2}$ with different affinities. NTA binds $Ni^{+2}$ with stronger affinity that IDA. A skilled artisan will be able to choose which binding affinity is desired for a particular application. The MPOD and affinity chromatography reagent can be linked by, for example, chemical cross linking. The cargo is linked to polyhistidine by any method known in the art for linking polyhistidine to small molecules, proteins, or nucleic acids. The MPOD-cargo domain complex can be formed by contacting the MPOD-affinity chromatography reagent complex with the polyhistidine-linked cargo domain in the presence of an ion such as $Ni^{+2}$.

A MPOD and cargo domain can be complexed chemically or using pairs of bridging molecules at any position on either the MPOD or the cargo domain, providing that functionality of either the MPOD or cargo domain is not destroyed. For example, a cross-linking agent will react with appropriate functional groups located at the amino-terminus or carboxy-terminus (for proteins), at the 5' end or 3' end (for nucleic acids), or throughout the small molecule. A skilled artisan will be able to determine if the respective parts of the MPOD-cargo domain complex retains biological activity. By way of example, the MPOD retains biological activity if it retains is ability to transport cargo into a cell. Transport activity can be ascertained, for example, by adding the MPOD cargo domain complex to cells and assaying the cells to determine if the cargo domain was delivered across the cell membrane. One skilled in the art can determine if the cargo is located intracellularly using methods well known in the art (e.g., immunohistochemical staining). The cargo domain can be assayed for activity using a method acceptable for the type of cargo domain (e.g., an enzyme assay for an enzyme, a transformation assay for an oncoprotein, an anti-apoptotic assay for an anti-apoptosis protein, and an immortalization assay for an immortalization protein). These assays are well known in the art and are described in Sambrook et al., 2012, Molecular Cloning: A Laboratory Manual, Cold Spring Harbor Laboratory, New York and Ausubel et al., 1997, Current Protocols in Molecular Biology, John Wiley & Sons, New York.

If the MPOD and polypeptide cargo domain are genetically linked, the polypeptide cargo domain can be complexed to either the amino terminus of the MPOD or to the carboxy-terminus of the MPOD.

MPODs of the invention can transport a cargo domain into a variety of mammalian, amphibian, reptilian, avian, or insect cells. Cells can be primary cells or cell lines. Mammalian cells can be, e.g., human, monkey, rat, mouse, dog, cow, pig, horse, hamster, and rabbit. Primary cells from mammalians include, but are not limited to, adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, ovary cells, pancreatic beta cells, renal cells, smooth muscle cells, and striated muscle cells.

Modified Peptidic Oligomer Mediated Cargo Delivery

The present invention relates to compositions and methods for promoting transduction of cargo molecules into the cytosol or nucleus of cells. In one embodiment, the modified peptidic oligomer composition serves to transduce the modified peptidic oligomer and at least one associated cargo molecule into cells. In one embodiment, an associated cargo molecule is covalently linked to a modified peptidic oligomer of the invention. In alternative embodiments, an associated cargo molecule is not covalently linked to the modified peptidic oligomer. For example, co-administration of the modified peptidic oligomer composition and a cargo molecule can result in delivery of the modified peptidic oligomer and at least one associated, non-covalently linked, cargo molecule to the cytosol or nucleus. Therefore, in one embodiment, the present invention relates to a composition comprising a modified peptidic oligomer, as described herein, and at least one cargo molecule. In one embodiment, the invention relates to a combination of a composition comprising a modified peptidic oligomer of the invention and a composition comprising at least one cargo molecule.

As described herein, components of the modified peptidic oligomer composition and at least one associated cargo molecule can be organized in nearly any fashion provided that the cargo has the function for which it was intended. In some embodiments, the cargo molecule may include tags, e.g., to facilitate detection, quantification, identification and/or purification of the fusion protein.

In some embodiments, the present invention is a nucleic acid encoding a modified peptidic oligomer and at least one associated cargo molecule of the invention. In certain embodiments, the invention comprises a nucleic acid molecule encoding at least two polypeptides, including a peptidic oligomer composition and at least one cargo molecule. In certain embodiments, the invention comprises at least two nucleic acid molecules encoding at least two polypeptides, including a peptidic oligomer composition and at least one cargo molecule.

In some embodiments, the modified peptidic oligomer composition and associated cargo described herein are produced by recombinant DNA techniques. For example, a DNA molecule encoding a peptidic oligomer composition can be ligated to another DNA molecule encoding the associated cargo polypeptide. In this instance, the resultant hybrid DNA molecule can be expressed in a suitable host cell to produce a peptidic oligomer composition and/or associated cargo. The DNA molecules are ligated to each other in a 5' to 3' orientation such that, after ligation, the translational frame of the encoded polypeptides is not altered (i.e., the DNA molecules are ligated to each other in-frame).

A polynucleotide can be inserted into an expression vector which contains the necessary elements for the transcription and translation of the inserted coding sequence. Transcription and translation control elements include, for example, a promoter (e.g., T7 or T3), ribosome binding site, start codon, stop codon, and polyadenylation site. Methods which are well known to those skilled in the art can be used to construct expression vectors containing sequences encoding the modified peptidic oligomer composition and associated cargo polypeptides and appropriate transcriptional and translational control elements. These methods include in vitro recombinant DNA techniques, synthetic techniques, and in vivo genetic recombination. Such techniques are described, for example, in Sambrook et al., 2012, Molecular Cloning: A Laboratory Manual, Cold Spring Harbor Laboratory, New York and in Ausubel et al., 1997, Current Protocols in Molecular Biology, John Wiley & Sons, New York.

A variety of expression systems are available for expressing sequences that encode the modified peptidic oligomer composition and associated cargo. Examples of such systems include, but are not limited to, bacteria, yeast, insect, plant, and animal cell systems. Bacteria can be transformed with recombinant bacteriophage, expression plasmids, or cosmid expression vectors. Yeast can be transformed with yeast expression vectors. Insect cells can be transfected with expression vectors or transduced with recombinant insect viruses (e.g., baculovirus). Plant cells can be transduced with recombinant plant viruses (e.g., cauliflower mosaic virus or tobacco mosaic virus). Animal cells can be transfected with expression vectors (e. g., pcDNA3 or pCMV-Sport) or transduced with recombinant viruses (e.g., retroviruses, adenoviruses, or semliki forest virus). Methods for transforming, transfecting, or transducing host cells are well-known in the art, and any appropriate method can be used.

A nucleic acid molecule can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al., 2012, Molecular Cloning: A Laboratory Manual, Cold Spring Harbor Laboratory, New York and other laboratory textbooks.

In one embodiment, the modified peptidic oligomer composition and associated cargo of the present invention are transduced into target cells or groups of such target cells. Transduction efficiency can be monitored and quantified if desired by one or a combination of different strategies. For example, one approach involves an in vitro assay that measures uptake of the modified peptidic oligomer composition and associated cargo by the cell. The assay includes detectably-labeling the modified peptidic oligomer composition, associated cargo, or both, with, e.g., a radioactive atom, fluorescent, phosphorescent, dexamethasone, or luminescent tag (e.g., fluorescein, rhodamine or FITC) and then measuring uptake of the labeled the modified peptidic oligomer composition or associated cargo. Alternatively, the modified peptidic oligomer composition, associated cargo, or both can be labeled with an enzyme capable of forming a detectable label such as horseradish peroxidase, P-galactosidase, chloramphenicol acetyl transferase or luciferase. In one embodiment, it is possible to genetically fuse a modified peptidic oligomer composition or associated cargo to florescent protein, such as green fluorescent protein (GFP), and then assay the location of the modified peptidic oligomer composition or associated cargo. Uptake can be measured by several conventional methods such as by quantifying labeled cells in a standard cell sorter (e.g., FACS), by fluorescence microscopy or by autoradiography.

The modified peptidic oligomer composition and associated cargo of the invention are capable of transducing at least about 5%, 10%, 20%, or more of the total number of target cells as determined by any methods for monitoring uptake of the fusion molecule by cells, such as FACS or related techniques. The total number of target cells can be estimated by standard techniques.

The modified peptidic oligomer composition and associated cargo can also be made by transcribing and translating a coding sequence in a cell-free expression system. A coding sequence for the modified peptidic oligomer composition and associated cargo can be linked to appropriate transcription and translation control elements by methods well known in the art. Examples of such methods include PCR, restriction enzyme digestion and ligation, and chemical synthesis. Such techniques are described, for example, in Sambrook et al., 2012, Molecular Cloning: A Laboratory Manual, Cold Spring Harbor Laboratory, New York and in Ausubel et al., 1997, Current Protocols in Molecular Biology, John Wiley & Sons, New York. Cell-free transcription and translation can be accomplished, for example, using components of rabbit reticulocyte or wheat germ extracts, which are available in kits from commercial suppliers such as Promega Corporation.

The peptidic oligomer composition and associated cargo can be purified from host cells or host cell culture medium by any method known in the art for purifying polypeptides. Examples of such methods include salt fractionation, high pressure liquid chromatography, antibody column chromatography, affinity tag column chromatography, and acrylamide gel electrophoresis. Such methods are well known to those skilled in the art.

The modified peptidic oligomer composition and associated cargo of the invention can contain conservative substitutions, i.e., exchange of one amino acid for another having similar properties. Examples of conservative substitutions include, but are not limited to, 1) glycine and alanine; 2) valine, isoleucine, and leucine; 3) aspartic acid and glutamic acid; 4) lysine and arginine; 5) asparagine and glutamine; and 6) serine and threonine.

The modified peptidic oligomer composition and associated cargo can be synthesized from D-or L-amino acids. In addition, use of amino acid analogs is also contemplated. Examples of amino acid analogs includes, but is not limited to, ethyl esters, methyl esters, naphthylamides, and 7-amido-4-methyl coumarin.

The modified peptidic oligomer composition, associated cargo, or both can also have a linker attached to the N-terminus or the C-terminus. The linker is usually 0, 1, 2, 3, 4, 5 or more amino acids in length and can be a small neutral polar or non-polar amino acid such as glycine, cysteine, serine, or threonine. An exemplary linker has an amino acid sequence Lys-Xaa-Xaa, wherein Xaa is a small neutral polar or nonpolar amino acid. In some embodiments, Xaa is glycine.

The cargo can be a small molecule (e.g., a radionuclide, a fluorescent marker, a dye, or a pharmaceutical agent), a protein (e.g., an immortalizing agent, an anti-apoptotic agent, an enzyme, an oncoprotein, a cell cycle regulatory protein, or an antibody), or a nucleic acid (e.g., RNA, DNA, and cDNA). Any of these cargo can be pharmaceutical agents. The small molecule also can be, for example, a radionuclide, a fluorescent marker, or a dye. A polypeptide according to the invention is a polymer of amino acids comprising two or more amino acid residues and includes peptides and proteins. The polypeptide can be, for example, an immortalization protein (e.g., SV40 large T antigen and telomerase), an anti-apoptotic protein (e.g., mutant p53 and Bclx L), an antibody, an oncogene (e.g., ras, myc, HPV E6/E7, and Adenovirus E1a), a cell cycle regulatory protein (e.g., cyclin and cyclin-dependent kinase), a zinc finger nuclease (ZFN), or an enzyme (e.g., green fluorescent protein, β-galactosidase, and chloramphenicol acetyl transferase). The nucleic acid can be, e.g., RNA, DNA, or cDNA. The sequence of the nucleic acid can be a coding or a non-coding sequence (e.g., an antisense oligonucleotide). Nucleotides in the nucleic acid cargo domain can be standard nucleotides (e.g., adenosine, cytosine, guanine, thymine, inosine, and uracil) or they can be nucleotide derivatives (e.g., biotinylated nucleotide) or analogs (e.g., phosphorothioate nucleotides). For example, the nucleic acid cargo can be an antisense sequence comprising phosphorothioate nucleotides.

Exemplary cargo will have sizes conducive to the function for which they are intended. In various embodiments, the cargo can be at least about 0.1, 0.2, 0. 5, 0.75, 1, 5, 10, 25, 30, 50, 100, 200, 500 kD, up to about 1000 kD or more.

In one embodiment, a cargo molecule can be complexed to the modified peptidic oligomer composition by any method known in the art and which is appropriate for a particular cargo. The skilled artisan will be able to choose the appropriate method to complex a cargo with the modified peptidic oligomer composition. In certain embodiments, the cargo is not covalently linked or attached to the modified peptidic oligomer composition. For example, in certain embodiments, the association of the modified peptidic oligomer composition and associated cargo involves various noncovalent interactions such as including hydrogen bonding, metal coordination, hydrophobic forces, van der Waals forces, pi-pi interactions, and/or electrostatic effects.

The modified peptidic oligomer composition and associated cargo of the present invention can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatograph, methods utilizing a difference in hydrophobicity such as reverse-phase high performance liquid chromatograph and methods utilizing a difference in isoelectric point, such as isoelectric focusing electrophoresis, metal affinity columns such as Ni-NTA. See generally Sambrook et al., 2012, Molecular Cloning: A Laboratory Manual, Cold Spring Harbor Laboratory Press and Ausubel et al., 1997, Current Protocols in Molecular Biology, John Wiley & Sons, New York for disclosure relating to these methods.

In some embodiments, the modified peptidic oligomer composition and associated cargo of the present invention are part of a substantially pure preparation. That is, the modified peptidic oligomer composition and associated cargo have been isolated from cell substituents that naturally accompany it so that the fusion proteins are present in at least 80% or 90% to 95% homogeneity (w/w). The modified peptidic oligomer composition and associated cargo having at least 98 to 99% homogeneity (w/w) are useful for many pharmaceutical, clinical and research applications. Once substantially purified the modified peptidic oligomer composition and associated cargo should be substantially free of contaminants for therapeutic applications. Once purified partially or to substantial purity, the modified peptidic oligomer composition and associated cargo can be used therapeutically, or in performing in vitro or in vivo assays. Substantial purity can be determined by a variety of standard techniques such as chromatography and gel electrophoresis.

The modified peptidic oligomer composition can transport a cargo into a variety of mammalian, amphibian, reptilian, avian, or insect cells. Cells can be primary cells or cell lines. Mammalian cells can be, e.g., human, monkey, rat, mouse, dog, cow, pig, horse, hamster, and rabbit. Primary cells from mammalians include, but are not limited to, adipocytes, astrocytes, cardiac muscle cells, chondrocytes, endothelial cells, epithelial cells, fibroblasts, gangliocytes, glandular cells, glial cells, hematopoietic cells, hepatocytes, keratinocytes, myoblasts, neural cells, osteoblasts, ovary cells, pancreatic beta cells, renal cells, smooth muscle cells, and striated muscle cells.

Pharmaceutical Compositions and Methods of Treatment

In various embodiments, the present invention is a method of treating a disease or disorder in a subject in need thereof, by administering to the subject, a modified peptidic oligomer, or a modified peptidic oligomer fusion molecule, as described elsewhere herein.

In various embodiments, the modified peptidic oligomers, or modified peptidic oligomer fusion molecules of the invention can be administered to cells in vitro, ex vivo, or in vivo, for example, by using a specified delivery mechanism suitable for introduction of into those cells. In general, the type of delivery mechanism selected will be guided by several considerations including the location of the cells, the degree of transduction needed to modulate a biologic activity within the cell, and the general health of the cells.

In particular, pharmaceutical compositions comprising at least one modified peptidic oligomer, and/or at least one modified peptidic oligomer fusion molecule of the invention may be administered to a mammal, particularly a primate such as a human, using a variety of suitable routes including oral, topical (including transdermal, buccal or sublingual), nasal and parenteral (including intraperitoneal, subcutaneous, intravenous, intradermal or intramuscular injection).

Formulations of the modified peptidic oligomers include those suitable for oral/nasal, topical, parenteral and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Methods of preparing these formulations or compositions include combining one compound and a carrier and, optionally, one or more accessory ingredients. In general, the formulations are prepared by combining a compound with a liquid carrier, or a finely divided solid carrier, or both, and then, if necessary, shaping the product.

Formulations of the modified peptidic oligomers, or modified peptidic oligomer fusion molecules, suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound as an active ingredient. A compound may also be administered as a bolus, electuary or paste. In solid dosage forms for oral administration (capsules, tablets, pills, dragees, powders, granules, and the like), a modified peptidic oligomer is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and/or (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of a modified peptidic oligomer include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds (e.g., modified peptidic oligomers), may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof. Methods of the invention can be administered topically in some embodiments, either to skin or to mucosal membranes (e.g., those on the cervix and vagina). This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration of a compound (e.g., a modified peptidic oligomer) include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a therapeutic compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Injectable depot forms are made by forming microencapsule matrices of the compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations of the compounds for intravaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Optionally, such formulations suitable for vaginal administration also include pessaries, tampons, creams, gels, pastes, foams or spray formulations containing such carriers as are known in the art to be appropriate.

The pharmaceutical compositions useful for practicing the invention may be administered to deliver a dose of between about 0.1 ng/kg/day and 100 mg/kg/day. In various embodiments, the pharmaceutical compositions useful in the methods of the invention may be administered, by way of example, systemically, parenterally, orally, or topically. In addition to the appropriate therapeutic composition, such pharmaceutical compositions may contain pharmaceutically acceptable carriers and other ingredients known to enhance and facilitate drug administration.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, parenteral, topical, intravenous, intramuscular, and other known routes of administration.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, and intramuscular.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

Typically dosages of the compound of the invention which may be administered to an animal, including but not limited to a human, range in amount from about 0.01 mg to about 100 g per kilogram of body weight of the animal. While the precise dosage administered will vary depending upon any number of factors, including, but not limited to, the type of animal and type of disease state being treated, the age of the animal and the route of administration. In various embodiments, the dosage of the compound will vary from about 1 mg to about 100 mg per kilogram of body weight of the animal. In other various embodiments, the dosage will vary from about 1 µg to about 1 g per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that the compositions of the invention, as discussed elsewhere herein, can be administered to a subject prior to the onset of the disease or disorder, thereby preventing the disease or disorder. The preventive methods described herein also include the treatment of a subject that is in remission for the prevention of a recurrence of a disease or disorder. One of skill in the art, when armed with the disclosure herein, would appreciate that the prevention of a disease or disorder encompasses administering to a subject a composition as a preventative measure against the disease or disorder.

In one embodiment, the method relates to administering a composition comprising a modified peptidic oligomer and a composition comprising at least one cargo molecule to a subject. A composition comprising a modified peptidic oligomer of the invention and a composition comprising at least one cargo molecule may be administered together or separately, and may be administered in any order and within any appropriate time frame for the modified peptidic oligomer and at least one associated cargo molecule to be delivered to the cytosol or nucleus of a cell. In one embodiment, a composition comprising a modified peptidic oligomer of the invention and a composition comprising at least one cargo molecule are administered concurrently. In one embodiment, a composition comprising a modified peptidic oligomer of the invention is administered less than 48 hours, less than 36 hours, less than 24 hours, less than 18 hours, less than 12 hours, less than 10 hours, less than 8 hours, less than 6 hours, less than 5 hours, less than 4 hours, less than 3 hours, less than 2 hours or less than 1 hour prior to or following administration of a composition comprising at least one cargo molecule.

Kits

Any of the compositions and methods described herein can be provided in the form of a kit. In various embodiments, a modified peptidic oligomer, a modified peptidic oligomer fusion molecule, and/or an MPOD and/or a cargo domain are supplied in a kit. The cargo domain can be a small molecule (e.g., a radionuclide, a fluorescent marker, a dye, or a pharmaceutical agent), a protein (e.g., an immortalizing agent, an anti-apoptotic agent, an enzyme, an oncoprotein, a cell cycle regulatory protein, or an antibody), or a nucleic acid (e.g., RNA, DNA, and cDNA). The MPOD and cargo domain can be supplied in single or divided aliquots, in single or divided containers. Written instructions can be included for assembling a MPOD-cargo domain complex and/or for using the complex. The instructions can be on the label or container. The instructions may simply refer a reader to another location such as a website or other information source.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out embodiments of the present invention, and are not to be construed as limiting in any way the remainder of the disclosure.

Example 1: Unique Arginine Array Improves Cytosolic Localization of Hydrocarbon-Stapled Peptides Here, is provided quantitative detail on the ability of diverse penta-arg motifs to facilitate the trafficking of certain peptide mimetics into the cell cytosol, and a distinct and unique penta-arg motif is identified that enhances the cytosolic access of an otherwise impermeant hydrocarbon-stapled peptide.

The materials and methods of this example are now described.

Materials

All purchased reagents were used without further purification. Standard Fmoc-protected amino acids were purchased from Novabiochem (San Diego, Calif.). Fmoc-protected olefinic amino acids, (S)—N-Fmoc-2-(4'-pentenyl) alanine and (R)—N-Fmoc-2-(7'-octenyl)alanine, were purchased from Okeanos Tech Jiangsu Co., Ltd (Jiangsu, P. R. China). Rink amide resin, N,N-dimethylformamide (DMF), N-hydroxybenzotriazole (HOBt), and Grubbs Catalyst™ 1st Generation were purchased from Sigma-Aldrich (St. Louis, Mo.). Trifluoroacetic acid (TFA) and dichloroethane (DCE) were purchased from Acros Organics (Fair Lawn, N.J.). N,N,N',N'-tetramethyl-uronium-hexafluorophosphate (HBTU), piperidine, and diisopropylethylamine (DIPEA) were purchased from AmericanBio (Natick, Mass.). 6-Chloro-benzotriazole-1-yloxy-tris-pyrrolidino-phosphonium hexafluorophosphate (PyClocK) was purchased from EMD Millipore (Billerica, Mass.). Acetic anhydride and Lissamine rhodamine B sulfonyl chloride were purchased from Fisher Scientific (Bridgewater, N.J.).

Peptide Synthesis

Peptides were synthesized using standard Fmoc chemistry with Rink amide resin on Biotage® Initiatior+Alstra from Biotage (Charlotte, N.C.) as previously described (LaRochelle et al., J. Am. Chem. Soc., 2015, 137, 2536-2541). Olefinic side-chain bearing residues were coupled and stapled for 2 hours at room temperature using PyClocK.

Fluorescence Correlation Spectroscopy

Cytosolic concentrations of rhodamine-labeled peptide in HeLa cells were determined using FCS as described previously (LaRochelle et al., J. Am. Chem. Soc., 2015, 137, 2536-2541). A 3D-anomalous diffusion model with background autocorrelation correction was used to fit averaged autocorrelation curves (Bernal et al., Cancer Cell, 2010, 18, 411-422).

Flow Cytometry

One day prior to experiments, 2 mL of HeLa cells at 50,000 cells/mL in clear DMEM supplemented with 10% FBS, 100 units/mL penicillin, and 100 µg/mL streptomycin were plated into 12-well Corning tissue culture treated plates and allowed to adhere overnight. The following day, the media was removed from adherent cells and 1 mL of 500 nM Rho-labeled peptides in clear DMEM was added for 30 minutes at 37° C. Cells were then washed three times with DPBS and lifted from the well with 300 µL 0.25% trypsin-EDTA or TrypLE, then diluted with 1.1 mL clear DMEM (with FBS) and pelleted at 800 g for 5 minutes. The supernatant was removed and 1.1 mL of DPBS was added, followed by pelleting at 500 g for 5 minutes. The supernatant was again removed and 300 µL of PBS was added to resuspend the cells. The cell suspension was kept on ice in an Eppendorf tube until measured on a FACS Aria (BD Biosciences, San Jose, Calif.) equipped with a 561 nm laser.

Cell Viability

SJSA-1 cells were seeded into a 96-well plate (2,000 cells/well) and incubated overnight at 37° C. After washing twice in PBS, cells are incubated with peptide or Nutlin-3a (Santa Cruz Biotechnology, Santa Cruz, Calif.) in Opti-MEM (Invitrogen, Carlsbad, Calif.) for 24 hours. Cell viability was then assayed using CellTiter-Glo (Promega, Madison, Wis.) according to the manufacturer's protocol. Luminescence measurements were taken on a SpectraMax M5 plate reader (Molecular Devices, Sunnyvale, Calif.).

The results of this example are now described.

Hydrocarbon-Stapled Peptides

Figures 3A, 3B, 3C, 3D:
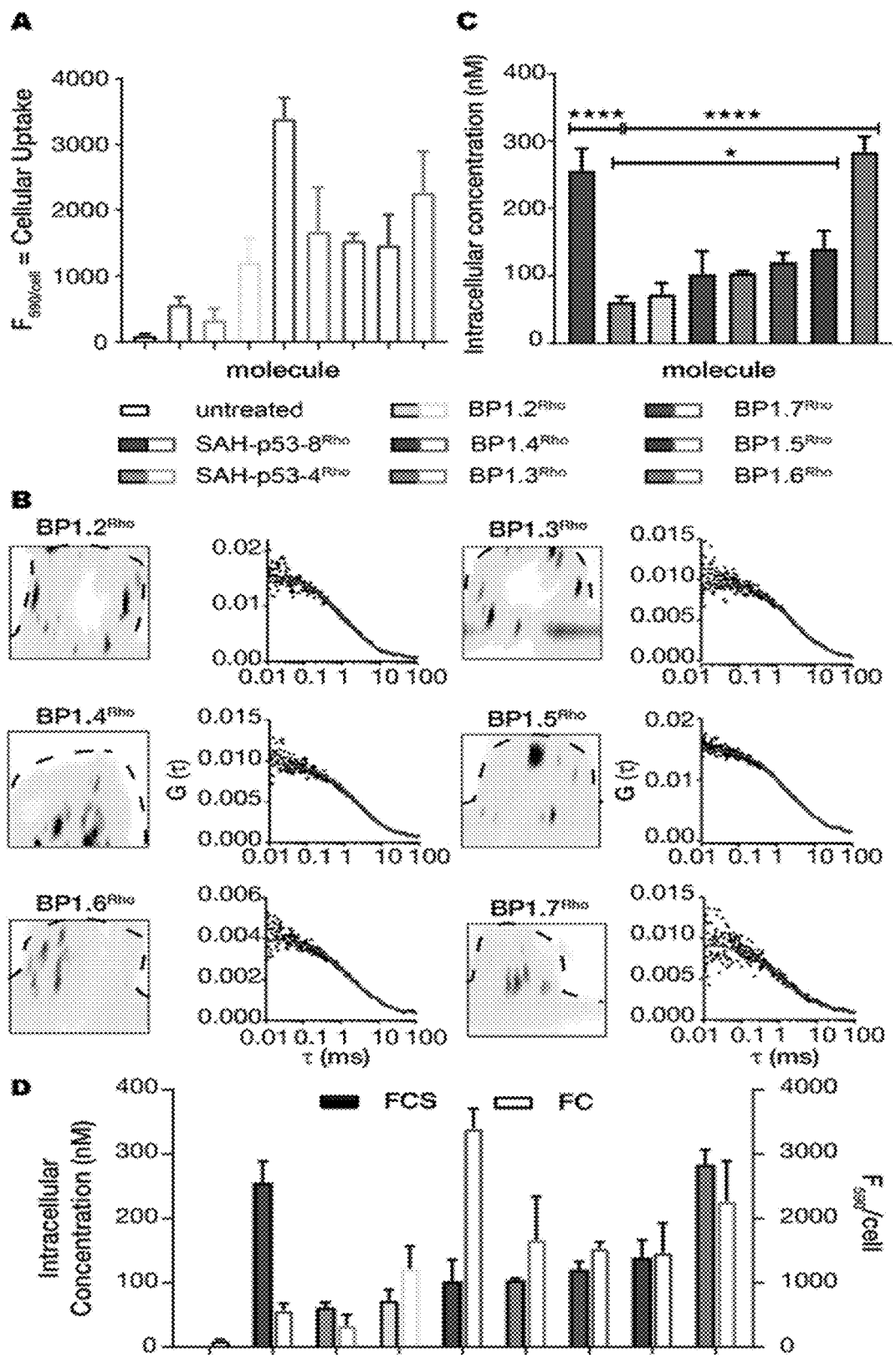
FIG. 3A through FIG. 3D, depicts the results of exemplary experiments demonstrating an assessment of overall uptake and cytosolic localization of second-generation SAH-p53-4 variants containing diverse penta-arg motifs.

SAH-p53-4, originally reported by Bernal et al. (FIG. 3A). SAH-p53-4 (Bernal et al., J. Am. Chem. Soc., 2007, 129, 2456-2457) is a hydrocarbon-stapled peptide that possesses high affinity for hDM2$_{17\text{-}125}$ ($K_D$=0.92±0.11 nM), a fragment of hDM2 that contains the p53 binding cleft, but, as judged by flow cytometry, fails to effectively breach the plasma membrane to reach endosomal compartments or the cytosol (Bernal et al., J. Am. Chem. Soc., 2007, 129, 2456-2457).

Figure 2:
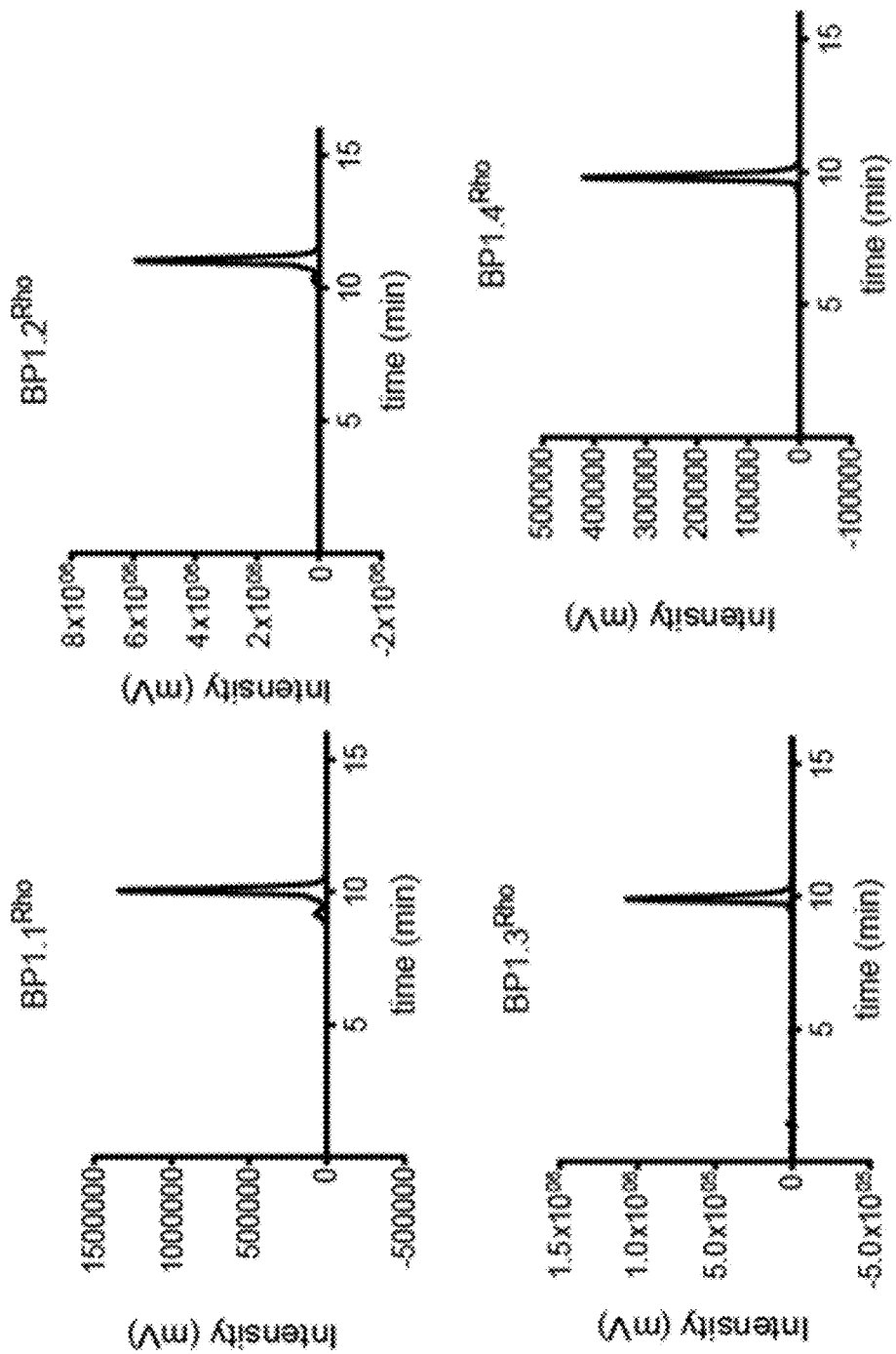
FIG. 2 depicts analytical HPLC traces of stapled peptides.
Figure 2:
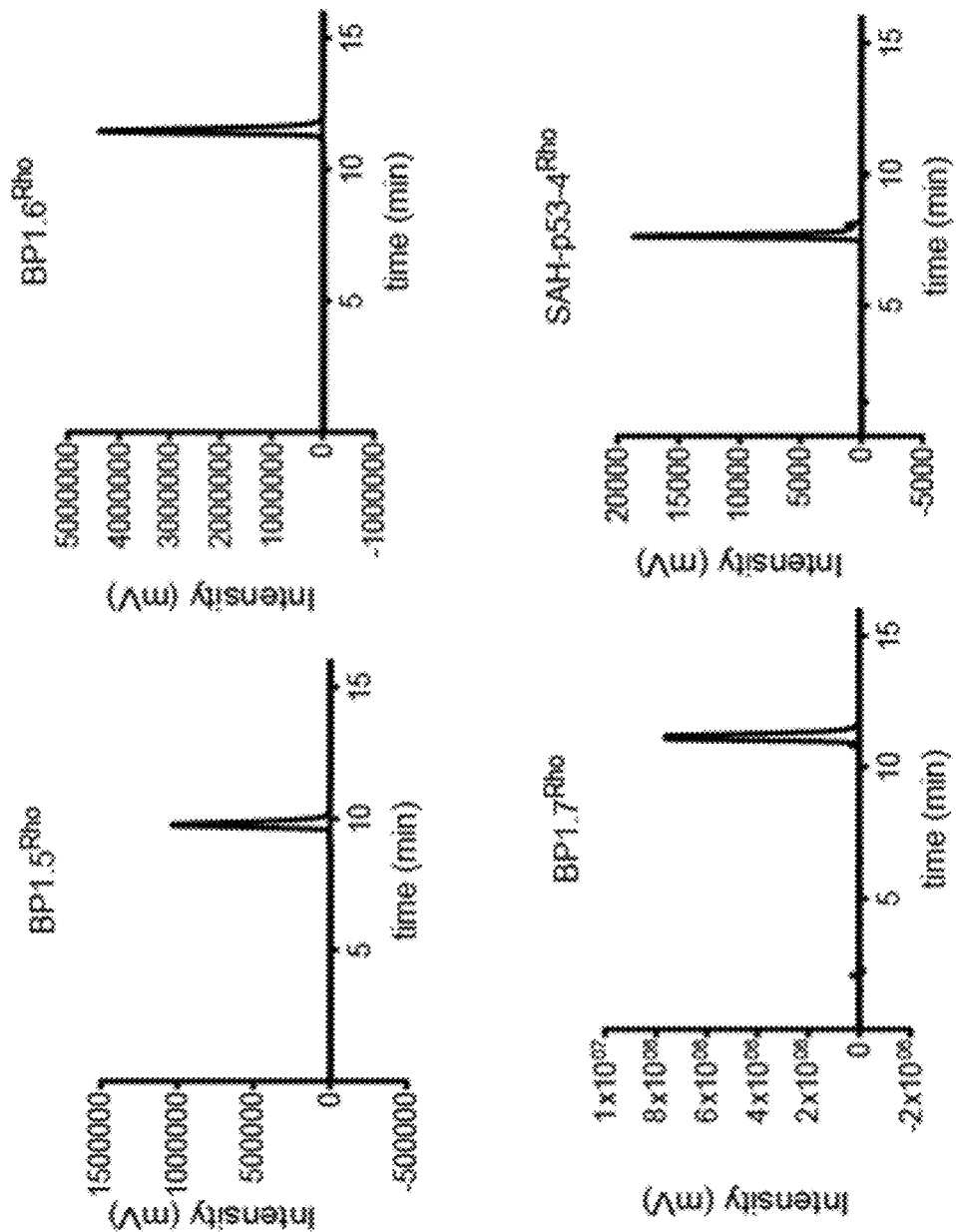
Figure 2:
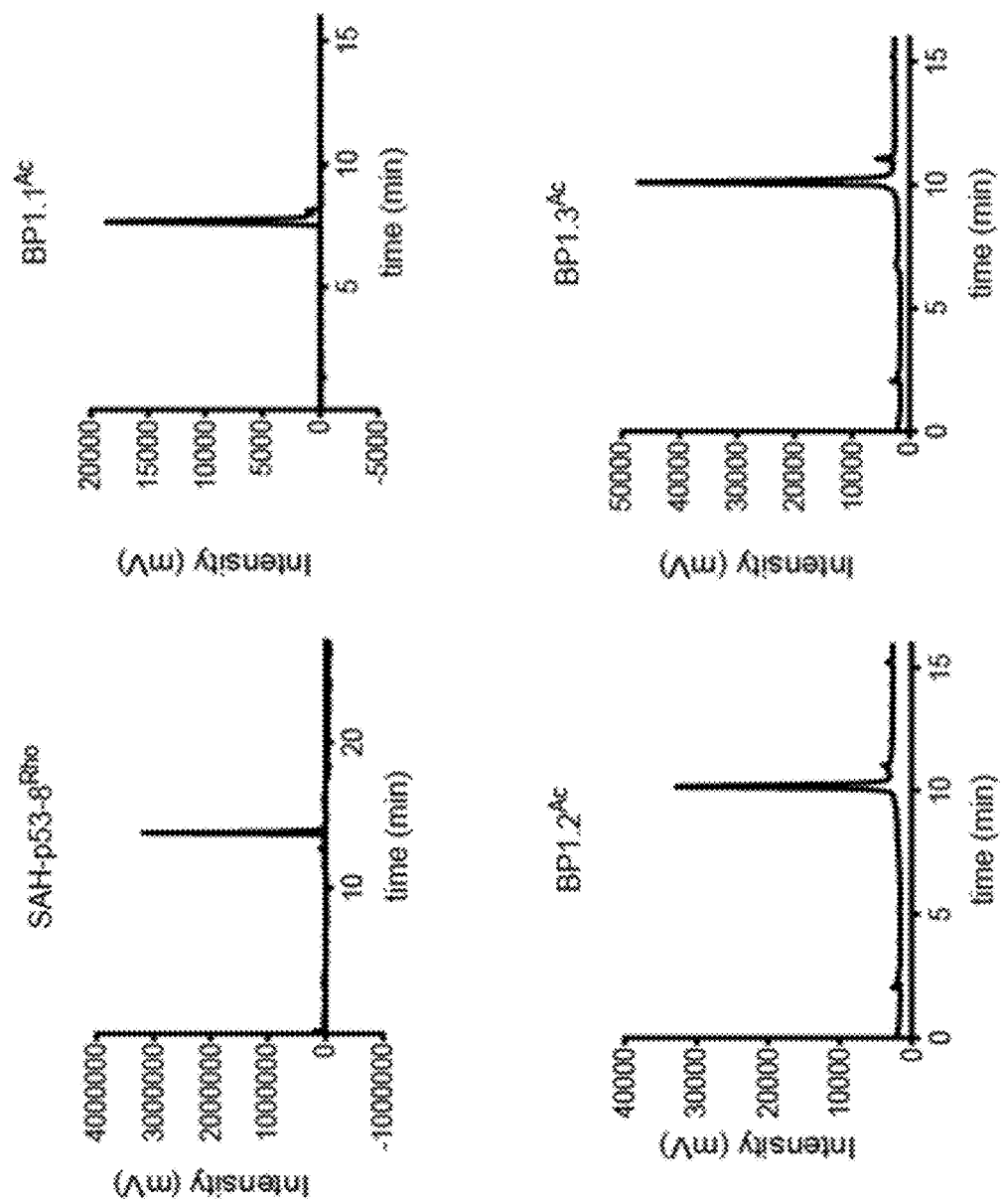
Figure 2:
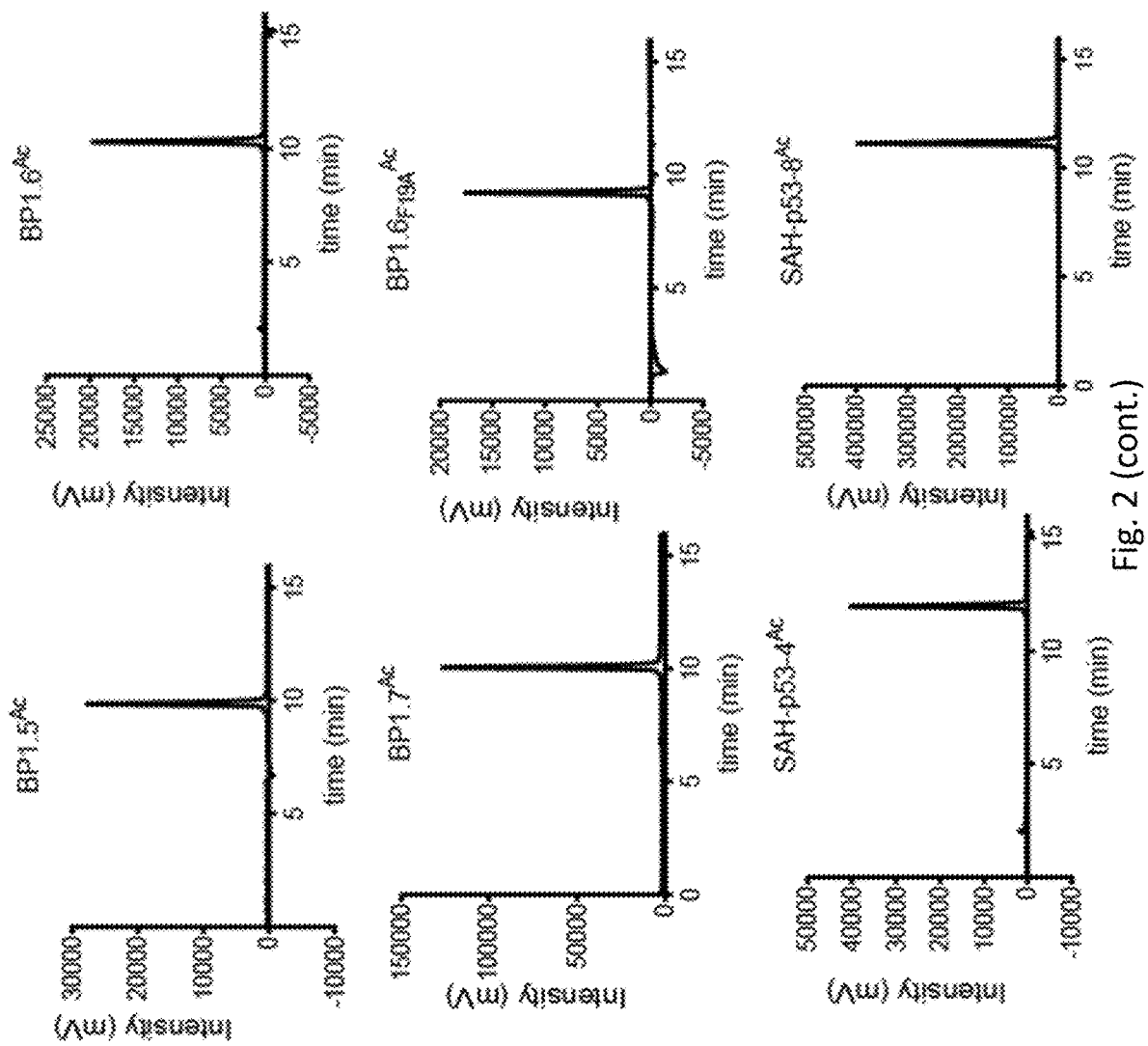

To evaluate whether the cytosolic access of SAH-p53-4 could be improved with a penta-arg motif, such as the penta-arg motif present in aPP5.3 and ZF5.3, variants of SAH-p53-4 were designed with arginine substitutions at various residues. While structural studies are scarce, it was recognized that the display of arginines on an α-helical scaffold may be affected by local, staple-induced changes in helix geometry, especially before the ligand engages its intracellular target. In other words, the arrangement of arginine side chains presented by aPP5.3 and ZF5.3 may not be identical to the arrangement when the same arginine pattern is embedded within SAH-p53-4. Therefore, various penta-arg arrays were developed to determine which was the most effective in the context of hydrocarbon-stapled peptides related to SAH-p53-4. A panel of six penta-arg variants of SAH-p53-4 that differed in both the relative spacing of five arginine residues and their axial arrangement was developed (FIG. 1). To ensure that any differences detected are due only to arginine arrangement and not electrostatics, all six of the new SAH-p53-4 variants carried an identical +4 net charge. To evaluate the role of relative position, the five arginine residues were either clustered on the same side of the helix (BP1.2, BP1.4, and BP1.6), or distributed around the helix (BP1.3, BP1.5, and BP1.7). To evaluate the role of axial position, different penta-arg motifs were clustered towards the N-terminus (BP1.2 and BP1.3), the C-terminus (BP1.6 and BP1.7), or dispersed throughout the peptide (BP1.4 and BP1.5). The relative positions of the five arginines in each peptide are depicted by helical wheel diagrams (FIG. 1), in which the dots representing arginine residues are circled. The i, i+7 staple and the hDM2 binding epitope were preserved. The variants were tagged on the N-terminus with Lissamine rhodamine B, and were synthesized following a modified version of the protocol reported by Bernal et al. (Bernal et al., J. Am. Chem. Soc., 2007, 129, 2456-2457); the purity of the final products was verified by analytical HPLC and the identity was confirmed by LC/MS (FIG. 2 and Table 1). Two previously reported molecules (Bernal et al., J. Am. Chem. Soc., 2007, 129, 2456-2457), SAH-p53-$4^{Rho}$ and SAH-p53-$8^{Rho}$, were prepared as negative and positive controls, respectively.

TABLE 1

LCMS data of stapled peptides

| SEQ ID NO: | Peptide | Sequence | Calculated m/z | Observed m/z |
|---|---|---|---|---|
| 1 | BP1.2$^{Rho}$ | Rho-βA-RSQRRFR$_8$RDWRLLS$_5$EN-NH$_2$ | 2833 | 2832 |
| 2 | BP1.3$^{Rho}$ | Rho-βA-RRRRRFR$_8$DLWKLLS$_5$EN-NH$_2$ | 2861 | 2860 |
| 3 | BP1.4$^{Rho}$ | Rho-βA-RSQERFR$_8$DLWKRLS$_5$RR-NH$_2$ | 2849 | 2848 |
| 4 | BP1.5R$^{ho}$ | Rho-βA-LRRETFR$_8$DRWKRLS$_5$RN-NH$_2$ | 2849 | 2848 |
| 5 | BP1.6$^{Rho}$ | Rho-βA-LSQETFR$_8$RLWRRLS$_5$RR-NH$_2$ | 2820 | 2819 |
| 6 | BP1.7$^{Rho}$ | Rho-βA-LRRETFR$_8$DLWKRLS$_5$RR-NH$_2$ | 2848 | 2847 |
| 7 | BP1.2$^{Ac}$ | Ac-RSQRRFR$_8$RDWRLLS$_5$EN-NH$_2$ | 2264 | 2263 |
| 8 | BP1.3$^{Ac}$ | Ac-RRRRRFR$_8$DLWKLLS$_5$EN-NH$_2$ | 2292 | 2292 |
| 9 | BP1.4$^{Ac}$ | Ac-RSQERFR$_8$DLWKRLS$_5$RR-NH$_2$ | 2280 | 2279 |
| 10 | BP1.5$^{Ac}$ | Ac-LRRETFR$_8$DRWKRLS$_5$RN-NH$_2$ | 2280 | 2279 |
| 11 | BP1.6$^{Ac}$ | Ac-LSQETFR$_8$RLWRRLS$_5$RR-NH$_2$ | 2251 | 2250 |
| 12 | BP1.7$^{Ac}$ | Ac-LRRETFR$_8$DLWKRLS$_5$RR-NH$_2$ | 2279 | 2278 |
| 13 | BP1.6$_{F19A}$$^{Ac}$ | Ac-LSQETAR$_8$RLWRRLS$_5$RR-NH$_2$ | 2174 | 2174 |
| 14 | SAH-p53-4$^{Rho}$ | Rho-βA-LSQETFR$_8$DLWKLLS$_5$EN-NH$_2$ | 2637 | 2638 |
| 15 | SAH-p53-8$^{Rho}$ | Rho-βA-QSQQTFR$_8$NLWKLLS$_5$QN-NH$_2$ | 2677 | 2678 |
| 16 | SAH-p53-4$^{Ac}$ | Ac-LSQETFR$_8$DLWKLLS$_5$EN-NH$_2$ | 2069 | 2069 |
| 17 | SAH-p53-8$^{Ac}$ | Ac-QSQQTFR$_8$NLWKLLS$_5$QN-NH$_2$ | 2109 | 2109 |

The set of Rho-labeled SAH-p53-4 variants, BP1.2$^{Rho}$-BP1.7$^{Rho}$, were evaluated first using flow cytometry to assess overall uptake (FIG. 3A). Although the set of molecules examined possessed the same overall charge, differing only in the relative placement of five arginine side chains, the overall uptake measured by flow cytometry varied more than three-fold. BP1.4$^{Rho}$, with five arginines along one face of the helix and dispersed along the peptide, exhibited the highest uptake, 2-3-fold higher than BP1.2$^{Rho}$, BP1.3$^{Rho}$, BP1.7$^{Rho}$ and BP1.5$^{Rho}$. BP1.2$^{Rho}$. All six new penta-arg peptides were taken up more efficiently than SAH-p53-4$^{Rho}$, with increases between 3.6- and 10-fold. This difference can likely be attributed to the greater net positive charge of the new penta-arg panel (+4) when compared to SAH-p53-4$^{Rho}$ which is negatively charged (−2). A similar trend was observed by Chu et al (Chu et al., Med. Chem. Commun., 2015, 6, 111-119).

The panel was next evaluated using FCS to identify those molecules that most effectively reached the cell interior, specifically the cytosol and nucleus. FCS is a unique tool for studying the trafficking of molecules across membranes as it provides a precise and accurate measure of the concentration of a fluorescently tagged molecule within the cytosol and/or the nucleus of a living cell. In contrast to flow cytometry, which measures total cell fluorescence—that is, fluorescence due to molecules within all cellular compartments, or even bound to the plasma membrane—FCS allows one to define with accuracy and precision the amount of material that reaches the cytosol and nucleus.

HeLa cells incubated with for 30 minutes with 500 nM of each Rho-labeled peptide were first washed extensively with buffer and trypsin until no plasma membrane-associated fluorescence could be detected using laser-scanning confocal microscopy. Cells were then placed on a home-built confocal imaging system and scanned along the x-z-dimensions to identify locations for focal volume placement within the cytosol that avoided regions with high punctate signal (FIG. 3B). Individual traces were assessed and averaged prior to fitting to a 3D autocorrelation function containing parameters for anomalous diffusion and background autocorrelation as described previously (LaRochelle et al., J. Am. Chem. Soc., 2015, 137, 2536-2541). The fluctuation in fluorescence intensity within the focal volume was measured and autocorrelated to extract concentration as described previously (LaRochelle et al., J. Am. Chem. Soc., 2015, 137, 2536-2541). Although SAH-p53-8$^{Rho}$ trafficked efficiently to the cytosol, achieving an intracellular concentration of 260±33 nM, SAH-p53-4$^{Rho}$ did not. These values correspond to trafficking efficiencies of 51.9% for SAH-p53-8$^{Rho}$ and 12.4% for SAH-p53-4$^{Rho}$, respectively. Evaluation of the correlation curves revealed that SAH-p53-4$^{Rho}$, SAH-p53-8$^{Rho}$, and the variants displayed wide variation in the maximal autocorrelation signal, indicating an equally wide variation in the concentration of each molecule in the cytosol.

Examination of the autocorrelation traces (FIG. 3B) or the calculated cytosolic concentration (FIG. 3C) reveals vast differences in the amount of material that reaches the cytosol and no correlation with overall uptake as measured by flow cytometry (FIG. 3D). For example, whereas BP1.4$^{Rho}$ is taken up efficiently by cells when evaluated by flow cytometry, FCS revealed that very little of that material reaches the cytosol. Just the opposite is observed when cells are treated with SAH-p53-8$^{Rho}$, although relatively little is taken up as judged by flow cytometry, a significant fraction of the material added to cells reaches the cytosol.

Closer evaluation of the FCS data provides additional insight into the factors required for efficient cytosolic access by hydrocarbon-stapled peptides. Overall, the six second-generation molecules showed wide variation in their ability to access the cytosol. As all molecules carried the same +4 charge, this variation is most likely due to arginine arrangement and/or differences in structure. BP1.6$^{Rho}$, with arginine residues at positions i, i+3, i+4, i+7, and i+8, accessed the cytosol most efficiently by far, reaching a final intracellular concentration of 284±23 nM. The cytosolic concentration of BP1.6$^{Rho}$ was virtually identical to that of SAH-p53-8$^{Rho}$ (256±33 nM) and significantly higher than any other member of the panel. It is noted that BP1.6$^{Rho}$ is the only second-generation molecule that lacked arginine residues on the N-terminal side of the hydrocarbon staple. Even when bound to MDM2, the residues of SAH-p53-8 in this region are too flexible be identified in the X-ray structure of the complex (PDB: 3V3B) (Baek et al., J Am Chem Soc, 2012, 134, 103-106). Given that the 5.3 motif is most effective when presented in a helical environment (Appelbaum et al., Chem. Biol., 2012, 19, 819-830; LaRochelle et al., J. Am. Chem. Soc., 2015, 137, 2536-2541), the higher activity of BP1.6$^{Rho}$ may result from the fact that it is the only member of the panel in which all residues are presented in a well-folded α-helical array. X-ray crystallographic studies of other hydrocarbon-stapled peptides also show that regions outside of the staple are not necessarily helical (Baek et al., J. Am. Chem. Soc., 2012, 134, 103-106; Bird et al., Nat. Struct. Mol. Biol., 2014, 21, 1058-1067; Chee et al., PLoS One, 2014, 9, e104914; Grossmann et al, Proc Natl Acad Sci USA, 2012, 109, 17942-17947; Lama et al., Sci Rep, 2013, 3, 3451; Phillips et al., J. Am. Chem. Soc., 2011, 133, 9696-9699; Speltz et al., Angew Chem Int Ed Engl, 2016, 55, 4252-4255). This observation suggests that for hydrocarbon-stapled peptides, the penta-arg motif should be positioned such that the maximum number of arginine residues are between or located in close proximity to the staple itself.

Cell Viability

Figure 4:
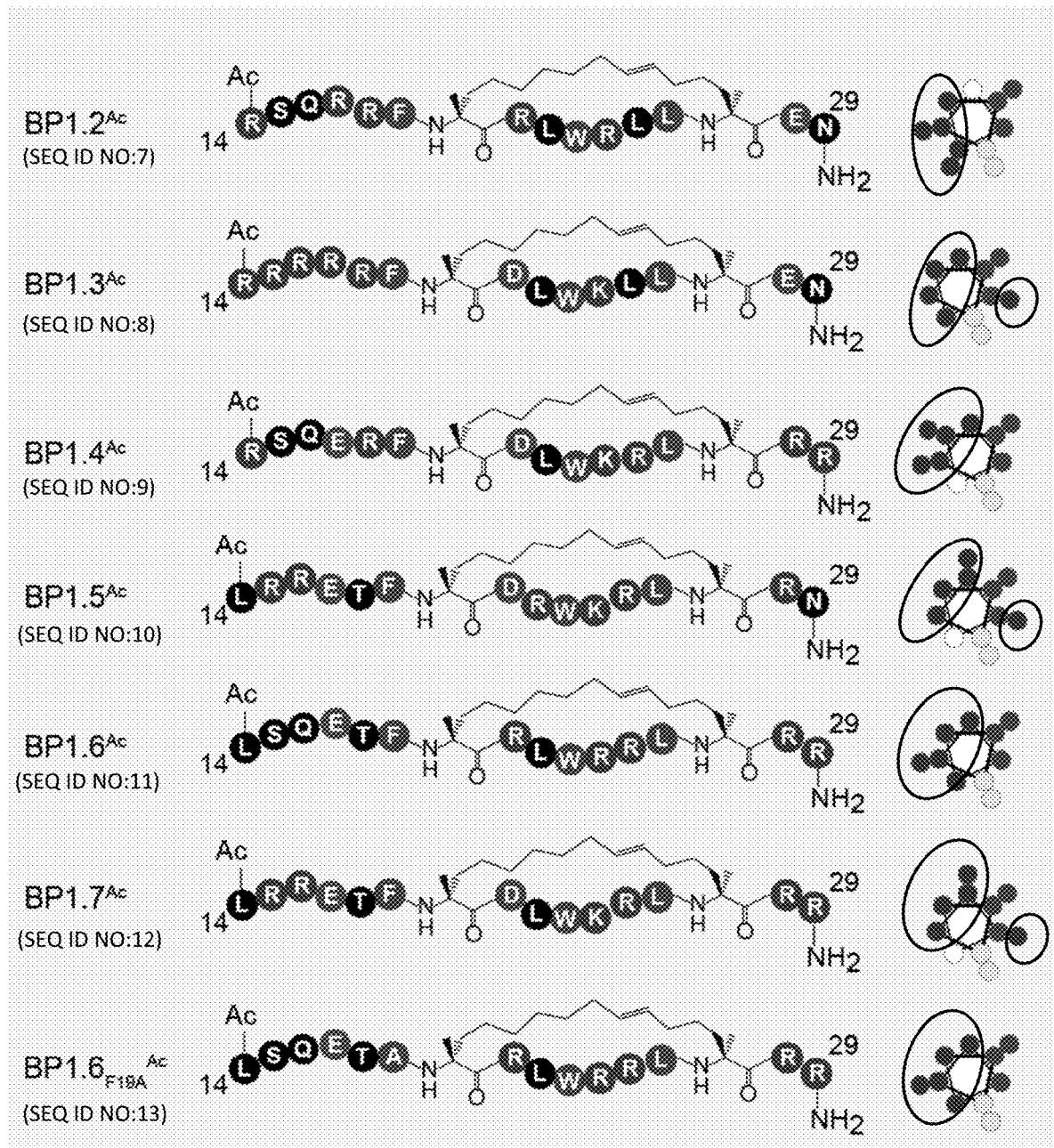
FIG. 4 depicts sequences of a set of N-acetylated second-generation panel of SAH-p53-4 variants containing diverse penta-arg motifs. The relative distribution of arginine residues (circled) is illustrated on the right with a helical wheel diagrams. The hydrocarbon staple and hDM2-binding epitope are denoted by filled uncircled dots.
Figure 5:
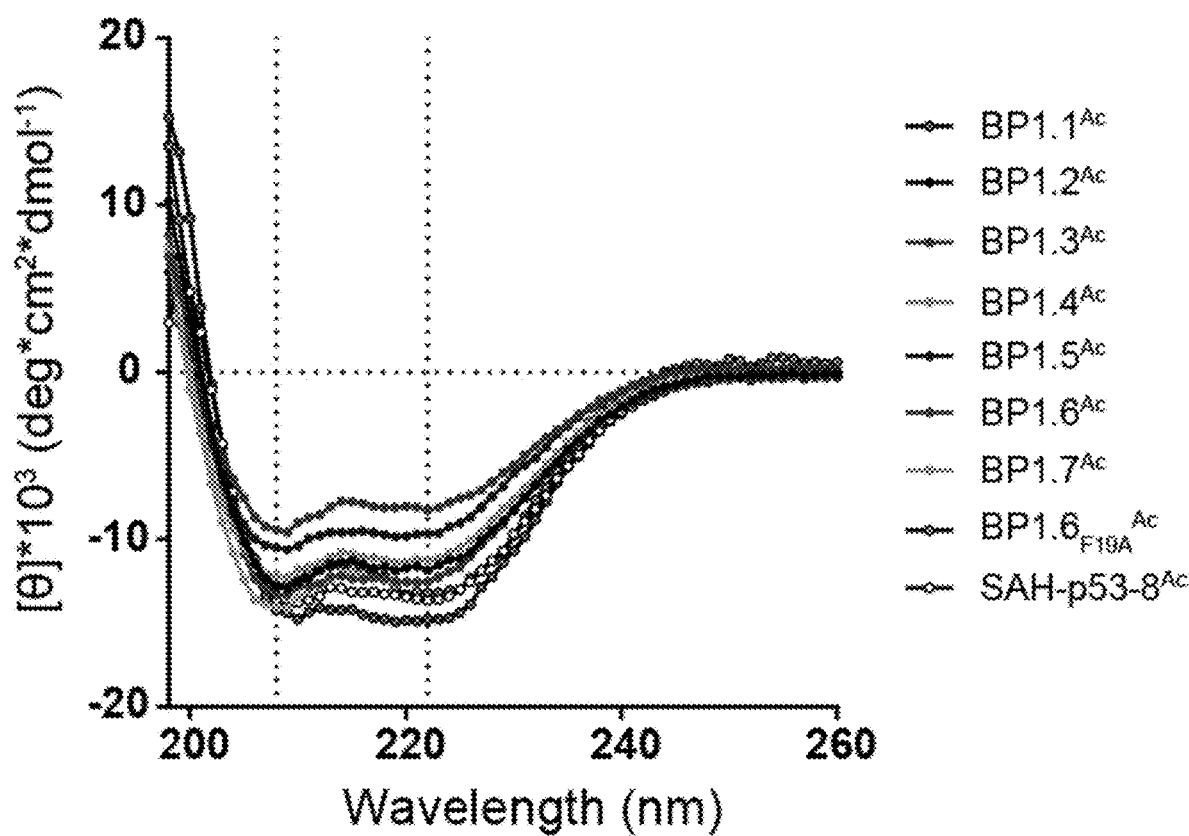
FIG. 5 depicts the results of exemplary experiments demonstrating circular dichroism of N-acetylated stapled peptides. Peptides were measured at 25 μM in DPBS.

Previously it has been shown that the efficacy with which hydrocarbon-stapled peptides reach the cytosol correlates with their efficacy in cell-based assays (LaRochelle et al., J. Am. Chem. Soc., 2015, 137, 2536-2541). To examine whether the biological activity of these penta-arg peptides correlated with how efficiently they accessed the cytosol, cell viability assays were performed using N-acetylated versions of the peptides and hDM2-overexpressing SJSA-1 cells (FIG. 4 and FIG. 5). As expected, treatment of SJSA-1 cells with SAH-p53-8$^{Ac}$ and Nutlin-3a resulted in dose-dependent decreases in viability, with ECso values of 10.2 µM and 22.75 µM, respectively; these values agree well with previously reported values of 8.8 µM (Bernal et al., J. Am. Chem. Soc., 2007, 129, 2456-2457) and ~7 µM (Bernal et al., Cancer Cell, 2010, 18, 411-422). Treatment of SJSA-1 cells with SAH-p53-4 led to no decrease in viability even at concentrations as high as 60 µM, also as expected (Bernal et al., J. Am. Chem. Soc., 2007, 129, 2456-2457).

Figure 6:
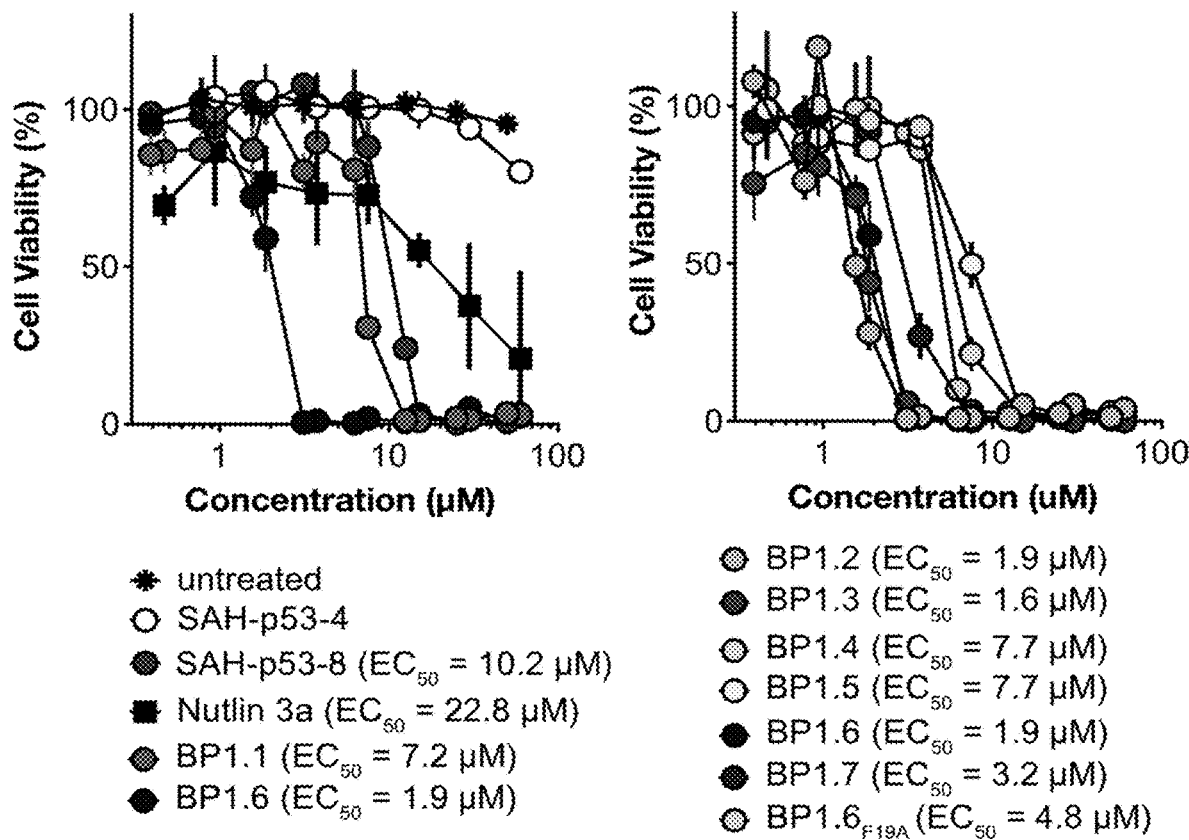
FIG. 6 depicts the results of exemplary experiments demonstrating the effect of penta-arg stapled peptides on the viability of SJSA-1 cells.

Examination of the effects of the remaining peptides on SJSA-1 cell viability reveals wide variability. All of the molecules studied were more potent than SAH-p53-8, with $EC_{50}$ values between 1.9 and 7.7 µM. BP1.2$^{Ac}$ and BP1.6$^{Ac}$ were the most potent ($EC_{50}$=1.9 µM), whereas BP1.4$^{Ac}$ and BP1.5$^{Ac}$ were the least potent ($EC_{50}$=7.7 µM) (FIG. 6). But there appears to be no relationship between potency in this assay and the efficiency with which each molecule reaches the cytosol. In order to determine whether the effect on cell viability was due to general cytotoxicity or varying affinities for hDM2, BP1.6$_{F19A}{}^{Ac}$ was synthesized, which contains a point mutation (F19A) that severely cripples hDM2 binding (Bernal et al., J. Am. Chem. Soc., 2007, 129, 2456-2457). Although BP1.6$_{F19A}{}^{Ac}$ should bind hDM2 poorly and not reactivate the p53 pathway, it still triggered a cytotoxic response in SJSA-1 cells ($EC_{50}$=4.8 µM). This observation suggests that while a penta-arg motif can be developed to enhance the cytosolic access of hydrocarbon-stapled peptides that engage hDM2, more work will be necessary to achieve the desired trafficking effects without cytotoxicity.

The results presented here found that a penta-arg motif with arginine residues at positions i, i+3, i+4, i+7, and i+8 was the most effective in trafficking to the cytosol. Importantly, there was no clear relationship between cellular uptake as judged by flow cytometry and cytosolic access as determined by FCS, emphasizing once again that to evaluate how much of given peptidic material reaches the cytosol, one must actually measure the concentration within the cytosol. These results suggest that for hydrocarbon-stapled peptides, the penta-arg motif should be positioned within more (as opposed to less) structured regions.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A modified peptidic oligomer comprising at least 5 cationic residues, wherein the at least 5 cationic residues are residues at positions i, i+3, i+4, i+7, and i+8 with respect to the first cationic residue, wherein the peptidic oligomer further comprises at least two unnatural amino acid residues selected from the group consisting of (R)-2-(7'-octenyl)alanine ($R_8$), (S)-2-(4'-pentenyl)alanine ($S_5$), (R)-2-(4'-pentenyl)alanine ($R_5$), and (S)-2-(7'-octenyl)alanine and a hydrocarbon staple formed between the two unnatural amino acid residues, and wherein the amino acid sequence of the peptidic oligomer is selected from the group consisting of SEQ ID NO:5 and SEQ ID NO:11.

2. The modified peptidic oligomer of claim 1, wherein the modified peptidic oligomer is incorporated into a fusion molecule comprising a modified peptidic oligomer domain (MPOD) and a cargo domain.

3. The fusion molecule of claim 2, wherein the cargo domain comprises at least one selected from the group consisting of a small molecule, a nucleic acid and a polypeptide.

4. The fusion molecule of claim 2, wherein the cargo domain is fused to the C-terminus of the MPOD.

5. The fusion molecule of claim 2, wherein the cargo domain is fused to the N-terminus of the MPOD.

6. The fusion molecule of claim 2, further comprising at least one selected from the group consisting of a linker and a label.

7. The modified peptidic oligomer of claim 6, wherein the label is a Rhodamine label.

8. A composition comprising a modified peptidic oligomer of claim 1 and at least one cargo molecule.

9. The composition of claim 8, wherein at least one cargo molecule comprises at least one selected from the group consisting of a small molecule, a nucleic acid and a polypeptide.

10. The composition of claim 8, wherein at least one cargo molecule is not covalently bound to the modified peptidic oligomer.

11. A method of promoting transduction of a cargo molecule into the cytosol or nucleus of a cell of a subject, the method comprising administering to the subject a therapeutically effective amount of the composition of claim 8.

12. The method of claim 11, wherein the subject is human.

13. A modified peptidic oligomer comprising at least 5 cationic residues, wherein the modified peptidic oligomer comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12.

* * * * *

SEQUENCE LISTING

<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Rhodamine label
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 1

Arg Ser Gln Arg Arg Phe Arg Arg Asp Trp Arg Leu Leu Ser Glu Asn
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Rhodamine label
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 2

Arg Arg Arg Arg Arg Phe Arg Asp Leu Trp Lys Leu Leu Ser Glu Asn
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Rhodamine label
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14

```
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 3

Arg Ser Gln Glu Arg Phe Arg Asp Leu Trp Lys Arg Leu Ser Arg Arg
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Rhodamine label
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 4

Leu Arg Arg Glu Thr Phe Arg Asp Arg Trp Lys Arg Leu Ser Arg Asn
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Rhodamine label
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 5

Leu Ser Gln Glu Thr Phe Arg Arg Leu Trp Arg Arg Leu Ser Arg Arg
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Rhodamine label
```

```
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 6

Leu Arg Arg Glu Thr Phe Arg Asp Leu Trp Lys Arg Leu Ser Arg Arg
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 7

Arg Ser Gln Arg Arg Phe Arg Leu Trp Arg Leu Leu Glu Asn
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 8

Arg Arg Arg Arg Arg Phe Arg Asp Leu Trp Lys Leu Leu Ser Glu Asn
1               5                   10                  15

<210> SEQ ID NO 9
<211> LENGTH: 16
```

```
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 9

Arg Ser Gln Glu Arg Phe Arg Asp Leu Trp Lys Arg Leu Ser Arg Arg
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 10

Leu Arg Arg Glu Thr Phe Arg Asp Arg Trp Lys Arg Leu Ser Arg Asn
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine
```

-continued

```
<400> SEQUENCE: 11

Leu Ser Gln Glu Thr Phe Arg Arg Leu Trp Arg Arg Leu Ser Arg Arg
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 12

Leu Arg Arg Glu Thr Phe Arg Asp Leu Trp Lys Arg Leu Ser Arg Arg
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 13

Leu Ser Gln Glu Thr Ala Arg Arg Leu Trp Arg Arg Leu Ser Arg Arg
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Rhodamine label
<220> FEATURE:
<221> NAME/KEY: MOD_RES
<222> LOCATION: (7)..(7)
<223> OTHER INFORMATION: (R)-2-(7'-octenyl)alanine
<220> FEATURE:
```

```
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 14

Leu Ser Gln Glu Thr Phe Arg Asp Leu Trp Lys Leu Leu Ser Glu Asn
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Rhodamine label
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 15

Gln Ser Gln Gln Thr Phe Arg Asn Leu Trp Lys Leu Leu Ser Gln Asn
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 16

Leu Ser Gln Glu Thr Phe Arg Asp Leu Trp Lys Leu Leu Ser Glu Asn
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Chemically Synthesized
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MISC_FEATURE
<222> LOCATION: (7)..(14)
<223> OTHER INFORMATION: R8S5 Peptide Staple, Linking residues 7 and 14
<220> FEATURE:
<221> NAME/KEY: MOD_RES
<222> LOCATION: (14)..(14)
<223> OTHER INFORMATION: (S)-2-(4'-pentenyl)alanine

<400> SEQUENCE: 17

Gln Ser Gln Gln Thr Phe Arg Asn Leu Trp Lys Leu Leu Ser Gln Asn
1               5                   10                  15
```